(12) United States Patent
Norberg et al.

(10) Patent No.: US 11,999,945 B2
(45) Date of Patent: *Jun. 4, 2024

(54) MODULATING POLYMER BEADS FOR DNA PROCESSING

(71) Applicant: Illumina, Inc., San Diego, CA (US)

(72) Inventors: Steven Norberg, La Mesa, CA (US); Dmitry K. Pokholok, San Diego, CA (US); Ramesh Ramji, San Diego, CA (US); Frank J. Steemers, Encinitas, CA (US); Fan Zhang, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 196 days.

This patent is subject to a terminal disclaimer.

(21) Appl. No.: 17/305,230

(22) Filed: Jul. 1, 2021

(65) Prior Publication Data

US 2021/0332349 A1  Oct. 28, 2021

Related U.S. Application Data

(63) Continuation of application No. 16/663,060, filed on Oct. 24, 2019, now Pat. No. 11,085,036.

(60) Provisional application No. 62/704,028, filed on Oct. 26, 2018.

(51) Int. Cl.
| | | |
|---|---|---|
| *C12N 15/10* | (2006.01) | |
| *B01L 3/00* | (2006.01) | |
| *C40B 30/00* | (2006.01) | |
| *C40B 60/02* | (2006.01) | |
| *C40B 80/00* | (2006.01) | |

(52) U.S. Cl.
CPC .... *C12N 15/1006* (2013.01); *B01L 3/502761* (2013.01); *C12N 15/1065* (2013.01); *C40B 30/00* (2013.01); *C40B 60/02* (2013.01); *C40B 80/00* (2013.01)

(58) Field of Classification Search
CPC ............ C12N 15/1006; C12N 15/1065; B01L 3/502761; C40B 30/00; C40B 60/02; C40B 80/00; B01J 13/046; B01J 13/203; B01J 13/22; B01J 13/206; C12Q 1/6806; C12Q 2563/149; C12Q 2563/159; C12Q 1/6869

See application file for complete search history.

(56) References Cited

U.S. PATENT DOCUMENTS

| | | | |
|---|---|---|---|
| 3,957,741 A | 5/1976 | Rembaum et al. | |
| 3,985,632 A | 10/1976 | Rembaum et al. | |
| 4,046,720 A | 9/1977 | Rembaum et al. | |
| 5,130,238 A | 7/1992 | Malek | |
| 5,185,243 A | 2/1993 | Ullman | |
| 5,455,166 A | 10/1995 | Walker | |
| 5,573,907 A | 11/1996 | Carrino | |
| 5,679,524 A | 10/1997 | Nikiforov | |
| 5,958,451 A | 9/1999 | Chen | |
| 6,210,891 B1 | 4/2001 | Nyren | |
| 6,214,587 B1 | 4/2001 | Dattagupta | |
| 6,258,568 B1 | 7/2001 | Nyren | |
| 6,274,320 B1 | 8/2001 | Rothberg | |
| 6,355,431 B1 | 3/2002 | Chee | |
| 6,890,741 B2 | 5/2005 | Fan | |
| 6,913,884 B2 | 7/2005 | Stuelpnagel | |
| 7,001,792 B2 | 2/2006 | Sauer | |
| 7,057,026 B2 | 6/2006 | Barnes | |
| 7,115,400 B1 | 10/2006 | Adessi | |
| 7,211,414 B2 | 5/2007 | Hardin | |
| 7,244,559 B2 | 7/2007 | Rothberg | |
| 7,315,019 B2 | 1/2008 | Turner | |
| 7,329,492 B2 | 2/2008 | Hardin | |
| 7,405,281 B2 | 7/2008 | Xu | |
| 7,582,420 B2 | 9/2009 | Oliphant | |
| 7,595,883 B1 | 9/2009 | Gamal | |
| 7,611,869 B2 | 11/2009 | Fan | |
| 7,670,810 B2 | 3/2010 | Gunderson | |
| 7,985,565 B2 | 7/2011 | Mayer | |
| 8,003,354 B2 | 8/2011 | Shen et al. | |
| 9,096,899 B2 | 8/2015 | Helmy et al. | |
| 9,388,465 B2 | 7/2016 | Hindson et al. | |
| 9,694,361 B2 | 7/2017 | Bharadwaj et al. | |
| 9,951,386 B2 | 4/2018 | Hindson et al. | |
| 11,085,036 B2 | 8/2021 | Norberg et al. | |
| 11,359,226 B2 | 6/2022 | Steemers et al. | |
| 2003/0006143 A1 | 1/2003 | Benerjee et al. | |
| 2003/0225173 A1 | 12/2003 | Albright et al. | |

(Continued)

FOREIGN PATENT DOCUMENTS

| | | |
|---|---|---|
| CA | 2622955 | 3/2007 |
| CA | 3047328 | 6/2018 |

(Continued)

OTHER PUBLICATIONS

Machine translation of JP4699207 in English published Jun. 8, 2011 (Year: 2011).*
Appleby et al. (Methods Mol Biol. 2009; 513:19-39).
Augst et al. Alginate hydrogels as biomaterials. Macromolecular Bioscience. 2006. 6: 623-633. (Year: 2006).
Bentley et al., Nature 456:53-59 (2008).
Bigdeli et al. A simple method for encapsulating single cells in alginate microspheres allows for direct PCR and whole genome amplification. PLoS One. 2015. 10(2): e011738. 15 pages. (Year: 2015).
Cockroft et al. J. Am. Chem. Soc. 130, 818-820 (2008).
Deamer et al. Acc. Chem. Res. 35:817-825 (2002).
Deamer et al. Trends Biotechnol. 18, 147-151 (2000).
Dean et al., Proc. Natl. Acad. Sci. USA 99:5261-66 (2002).

(Continued)

*Primary Examiner* — Narayan K Bhat
(74) *Attorney, Agent, or Firm* — Knobbe, Martens, Olson & Bear, LLP

(57) ABSTRACT

Systems, methods, and compositions provided herein relate to preparation of beads encapsulating biomolecules for performing sequential reactions on the biomolecules. Some embodiments include preparation of nucleic acid reactions within the bead, wherein the bead includes pores that allow diffusion of molecules into or out of the beads while retaining other molecules of interest.

24 Claims, 25 Drawing Sheets

Specification includes a Sequence Listing.

(56) References Cited

U.S. PATENT DOCUMENTS

| | | |
|---|---|---|
| 2005/0053980 A1 | 3/2005 | Gunderson |
| 2005/0181440 A1 | 8/2005 | Chee |
| 2005/0191698 A1 | 9/2005 | Chee |
| 2006/0013784 A1 | 1/2006 | Philippe et al. |
| 2008/0108082 A1 | 5/2008 | Rank |
| 2008/0182287 A1 | 7/2008 | Smith |
| 2009/0026082 A1 | 1/2009 | Rothberg |
| 2009/0127589 A1 | 5/2009 | Rothberg |
| 2009/0186349 A1 | 7/2009 | Gunderson |
| 2010/0136544 A1 | 6/2010 | Agresti et al. |
| 2010/0137143 A1 | 6/2010 | Rothberg |
| 2010/0282617 A1 | 11/2010 | Rothberg |
| 2012/0129954 A1 | 5/2012 | Falcone et al. |
| 2012/0208255 A1 | 8/2012 | Andersen et al. |
| 2013/0011441 A1 | 1/2013 | Hollinger et al. |
| 2014/0228255 A1 | 8/2014 | Hindson et al. |
| 2015/0071997 A1 | 3/2015 | Garcia et al. |
| 2015/0157569 A1 | 6/2015 | Shum et al. |
| 2015/0284768 A1 | 10/2015 | Craig et al. |
| 2015/0376609 A1 | 12/2015 | Hindson et al. |
| 2016/0122804 A1 | 5/2016 | Smith et al. |
| 2016/0271064 A1 | 9/2016 | Sell et al. |
| 2019/0249171 A1 | 8/2019 | Wu et al. |
| 2022/0411859 A1 | 1/2022 | Wu et al. |
| 2022/0106588 A1 | 4/2022 | Wu et al. |
| 2022/0333157 A1 | 10/2022 | Steemers et al. |

FOREIGN PATENT DOCUMENTS

| | | |
|---|---|---|
| CN | 101514956 | 8/2009 |
| CN | 101838696 | 9/2010 |
| CN | 101845494 | 9/2010 |
| CN | 102102122 | 6/2011 |
| CN | 103328981 | 9/2013 |
| CN | 104471075 | 3/2015 |
| CN | 105412935 | 3/2016 |
| CN | 105431554 | 3/2016 |
| CN | 105492607 | 4/2016 |
| CN | 105916689 | 8/2016 |
| CN | 106536734 | 3/2017 |
| CN | 106769336 | 5/2017 |
| CN | 107002117 | 8/2017 |
| CN | 108165119 | 6/2018 |
| EP | 0320308 | 6/1989 |
| EP | 0336731 | 10/1989 |
| EP | 0439182 | 7/1991 |
| JP | 2003-519565 | 6/2003 |
| JP | 2004-507488 | 3/2004 |
| JP | 2007-112754 | 5/2007 |
| JP | 2007-514518 | 6/2007 |
| JP | 4699207 B2 * | 6/2011 ........... B01D 67/003 |
| JP | 2016-517281 | 6/2016 |
| JP | 2016-519079 | 6/2016 |
| JP | 2017-510292 | 4/2017 |
| JP | 2018-528291 | 9/2018 |
| JP | 2020-518292 | 6/2020 |
| JP | 2020-532948 | 11/2020 |
| KR | 10-2017-0020704 | 2/2017 |
| RU | 2274863 C2 | 4/2006 |
| RU | 2603745 | 11/2016 |
| WO | WO 1989/09835 | 10/1989 |
| WO | WO 1989/12696 | 12/1989 |
| WO | WO 1990/01069 | 2/1990 |
| WO | WO 1991/006678 | 5/1991 |
| WO | WO 95/23875 | 9/1995 |
| WO | WO 200002018 | 1/2000 |
| WO | WO 2001/051196 | 7/2001 |
| WO | WO 2002/017888 | 3/2002 |
| WO | WO 03/079401 | 9/2003 |
| WO | WO 2004/018497 | 6/2004 |
| WO | WO 05/021755 | 3/2005 |
| WO | WO 05/021804 | 3/2005 |
| WO | WO 2005/032512 | 4/2005 |
| WO | WO 2006/125458 | 11/2006 |
| WO | WO 07/114758 | 10/2007 |
| WO | WO 2007/123744 | 11/2007 |
| WO | WO 08/045806 | 4/2008 |
| WO | WO 2008/109176 | 9/2008 |
| WO | WO 11/123246 | 10/2011 |
| WO | WO 11/156432 | 12/2011 |
| WO | WO 2012/058096 | 5/2012 |
| WO | WO 14/152673 | 9/2014 |
| WO | WO 14/153126 | 9/2014 |
| WO | WO 2014/145555 | 9/2014 |
| WO | WO 2014/189957 | 11/2014 |
| WO | WO 2015/048173 | 4/2015 |
| WO | WO 2015/088299 | 6/2015 |
| WO | WO 15/121434 | 8/2015 |
| WO | WO 2015/147147 | 10/2015 |
| WO | WO 2015/200893 | 12/2015 |
| WO | WO 16/004068 | 1/2016 |
| WO | WO 2016/004234 | 1/2016 |
| WO | WO 2016/130704 | 8/2016 |
| WO | WO 16/160475 | 10/2016 |
| WO | WO 2017/013138 | 1/2017 |
| WO | WO 2017/040024 | 3/2017 |
| WO | WO 17/075072 | 5/2017 |
| WO | WO 2017/075265 | 5/2017 |
| WO | WO 2017/100347 | 6/2017 |
| WO | WO 2018/071448 | 4/2018 |
| WO | WO 18/118971 | 6/2018 |
| WO | WO 2018/119301 | 6/2018 |
| WO | WO 2018/140966 | 8/2018 |
| WO | WO 18/172726 | 9/2018 |
| WO | WO2018/203141 | 11/2018 |
| WO | WO 2019/028047 | 2/2019 |
| WO | WO 2019/028166 | 2/2019 |
| WO | WO 2019/160820 | 8/2019 |
| WO | WO 20/112604 | 6/2020 |
| WO | WO 20/165433 | 8/2020 |
| WO | WO 20/167866 | 8/2020 |

OTHER PUBLICATIONS

Decision to Grant issued in RU application No. 2019144343, dated Apr. 27, 2021.

Fox et al. (Methods Mol Biol. 2009;553:79-108).

Freeman et al: "Single-cell genome sequencing at ultra-high-throughput with microfluidic droplet barcoding. (includes Online Methods)", 1-7, 24-33, Nature Biotechnology, vol. 35, No. 7, Jul. 1, 2017 (Jul. 1, 2017) pp. 640-646, 4pp.

Garni, Biopores/membrane proteins in synthetic polymer membranes, Biochimica et Biophysica Acta, 1859, 2017, 619-638.

Grothues et al. Nucleic Acids Res. 21(5):1321-2 (1993).

Healy, Nanomed. 2, 459-481 (2007).

International Search Report and Written Opinion issued in patent application No. PCT/US2019/027540, dated Jul. 24, 2019.

International Search Report issued in application No. PCT/US2018/044855, dated Oct. 15, 2018.

Korlach et al. Proc. Natl. Acad. Sci. USA 105, 1176-1181 (2008).

Kumachev et al., "High-throughput generation of hydrogel microbeads with varying elasticity for cell encapsulation", Biomaterials, Elsevier Science Publishers BV., Barking, GB, (Feb. 1, 2011), pp. 1477-1483.

Lage et al., Genome Research 13:294-307 (2003).

Levene et al. Science 299, 682-686 (2003).

Li et al. Nat. Mater. 2:611-615 (2003).

Lizardi et al., Nat. Genet. 19:225-232 (1998).

Lundquist et al. Opt. Lett. 33, 1026-1028 (2008).

Margulies et al. (Nature 2005 437: 376-80).

Morozova et al. (Genomics. 2008 92:255-64).

Novak et al., "Single-cell multiplex gene detection and sequencing with microfluidically generated agarose emulsions", Wiley—VCH Verlag GMBH & co, DE, vol. 50, No. 2, Jan. 10, 2011 (Jan. 10, 2011), pp. 390-395.

Office Action issued in EP application No. 18755643.6, dated May 10, 2021.

Office Action issued in JP application No. 2019-568626, dated Feb. 2, 2021.

(56) References Cited

OTHER PUBLICATIONS

Office Action issued in JP application No. 2019-568626, dated Jun. 22, 2021.
Picelli et al., "Tn5 transposase and tagmentation procedures for massively scaled sequencing projects", Genome Research, vol. 24, No. 12, Jul. 30, 2014 (Jul. 30, 2014), pp. 2033-2040.
Pregibon et al., "Optimization of Encoded Hydrogel Particles for Nucleic Acid Quantification", Analytical Chemistry, vol. 81, No. 12, Jun. 15, 2009 (Jun. 15, 2009), pp. 4873-4881.
Rakszewska et al. (Angewandte Chemie, 2016, 55:6698-6701) (Year: 2016).
Ronaghi et al. (Analytical Biochemistry 1996 242: 84-9).
Ronaghi et al. Science 281(5375), 363 (1998).
Ronaghi, Genome Res. 11(1), 3-11 (2001).
Search Report and Written Opinion issued in application No. PCT/US2019/057852, dated Jan. 16, 2020.
Search Report issued in AU application No. 2018312560, dated Mar. 11, 2021.
Search Report issued in AU application No. 2019220559, dated Mar. 12, 2021.
Search Report issued in AU application No. 2019220559, dated May 19, 2021.
Search Report issued in RU application No. 2019144343, dated Jun. 21, 2020.
Shendure et al. (Science 2005 309: 1728-32).
Shupletsova et al., "Encapsulation of cells and tissues of the pancreas: problems and ways to overcome them", Genes and cells, vol. XI, N 1, 2016, pp. 18-23.
Soni et al. Clin. Chem. 53, 1996-2001 (2007).
Tan et al, Heterogeneous multi-compartmental hydrogel particles as synthetic cells for incompatible tandem reactions, 2017, Nature Communications, 8,663, pp. 1-10 (Year: 2017).
Trivedi et al. Microfluidic encapsulation of cells in alginate capsules for high throughput screening. 31st Annual International Conference of the IEEE EMBS. Minneapolis, Minnesota, USA. Sep. 2-6, 2009. 2009: 7037-7040. (Year: 2009).
Vitak et al. Nat Meth. 2017;14:302-308.
Walker et al., Nucl. Acids Res. 20:1691-96 (1992).
Office Action issued in JP application No. 2022-021757, dated Mar. 7, 2023.
Elbert, DL et al. Protein delivery from materials formed by self-selective conjugate additions reactions. Journal of Controlled Release. 2001. 76: 11-25. (Year: 2001).
Boeke et a., 1989, Transcription and reverse transcription of retrotransposons, Annu Rev Microbiol. 43:403-434.
Brown et al., 1989, Retroviral integration: structure of the initial covalent product and its precursor, and a role for the viral IN protein, Proc Natl Acad Sci USA, 86:2525-2529.
Colegio et al., 2001, In vitro transposition system for efficient generation of random mutants of campylobacter jejuni, J. Bacteriol., 183(7):2384-2388.
Craig, 1996, Transposon Tn7, Review in: Curr Top Microbiol Immunol., 204:27-48.
Craig, Mar. 15, 1996, V(D)J recombination and transposition: closer than expected Science. 271:1512.
Devine et al., 1994, Efficient integration of artificial transposons into plasmid targets in vitro: a useful tool for DNA mapping, sequencing and genetic analysis, Nucleic Acids Res., 22(18):3765-3772.
Gloor, 2004, Gene targeting in *Drosophila*, Methods Mol. Biol., 260:97-114.
Goryshin et al., Mar. 27, 1998, Tn5 in vitro transposition, J. Biol. Chem. 273:7367-7374.
Ichikawa et al., Nov. 5, 1990, In vitro transposition of Transposon Tn3*, J. Biol. Chem., 265:18829-18832.

Kirby et al., 2002, Cryptic plasmids of *Mycobacterium avium*: Tn552 to the rescue, Mol. Microbiol., 43(1):173-186.
Kleckner et al., 1996, Tn10 and IS10 transposition and chromosome rearrangements: mechanism and regulation in vivo and in vitro, Curr. Top. Microbiol. Immunol., 204:49-82.
Lampe et al., 1996, A purified mariner transposase is sufficient to mediate transposition in vitro, EMBO J., 15:5470-5479.
Mizuuchi, Dec. 1983, In vitro transposition of bacteriophage mu: a biochemical approach to a novel replication reaction, Cell, 35:785-794.
Ohtsubo 1996, Bacterial insertion sequences, Curr. Top. Microbiol. Immunol. 204:1-26.
Plasterk, 1996, The Tc1/mariner transposon family, Curr. Top. Microbiol. Immunol., 204:125-143.
Savilahti et al., 1995, The phage mu transposone core: DNA requirements for assembly and function, EMBO J., 14:4893-4903.
Wikipedia, Polyethylene glycol, 8 pages, revision date Jul. 4, 2016 by user "Anypodetos". [Retrieved on Jul. 25, 2023]. Retrieved from Internet: <URL:https://en.wikipedia.org/w/index.php?title=Polyethylene_glycol&oldid=728284755>, 8 pp.
Wilson et al., 2007, New transposon delivery plasmids for insertional mutagenesis in bacillus anthracis, J. Microbiol. Methods, 71:332-335.
Zhang et al., Oct. 2009, A novel mechanism of transposon-mediate gene activation, PLoS Genet. 5(10):e1000689.
Office Action issued in RU application No. 2021118349, dated Sep. 14, 2022.
Ramli, Ros Azlinawati,et al., "Core-shell polymers: a review", RSC Adv., 2013, 3, 15543-15565.
Notice of Allowance issued in RU application No. 2021118349, dated Feb. 3, 2023.
Avens et al., Oct. 17, 2008, Polymerization behavior and polymer properties of eosin-mediated surface modification reactions, Polymer (Guildf), 49(22):4762-4768.
Brandl et al., 2007, Rational design of hydrogels for tissue engineering: impact of physical factors on cell behavior. Biomaterials. 28:134-146.
Chen et al. Sep. 10, 2012, Low modulus biomimetic microgel particles with high loading of hemoglobin. Biomacromolecules, 13(9):2748-2759.
Cruise et al., 1998, Characterization of permeability and network structure of interfacially photopolymerized poly(ethylene glycol) diacrylate hydrogels, Biomaterials, 19:1287-1294.
Imelfort et al., 2009, De novo sequencing of plant genomes using second-generaiton technologies, Brief Bioinform, 10(6):609-618.
Ioannidis, 2009, Manufacturing of agarose-based chromatographic adsorbents with controlled pore and particle size, a thesis submitted to the University of Birmingham for the degree of Doctor of Philosophy, 214 pp.
Kapur et al., 1996, Hydrodynamic permeability of hydrogels stabilized within porous membranes. Industrial & Engineering Chemistry Research, 35:3179-3185.
Seidlits et al., 2010, The effects of hyaluronic acid hydrogels with tunable mechanical properties on neural progenitor cell differentiation, Biomaterials, 31:3930-3940.
Walker et al., 1995, A chemiluminescent DNA probe test based on strand displacement amplification, in Wsiedbrauk et al., eds., Molecular Methods for Virus Detection, Academic Press, Inc., pp. 330 349.
Weber et al., Sep. 1, 2009. Effects of PEG hydrogel crosslinking density on protein diffusion and encapsulated islet survival and function, Journal of Biomedical Materials Research Part A. 90:720-729.
Examination report dated Jun. 6, 2023 in Indian patent application No. 202117010489.
Office Action dated Apr. 24, 2023 in Russian patent application No. 2021108033/04(017322), 17 pp.

* cited by examiner

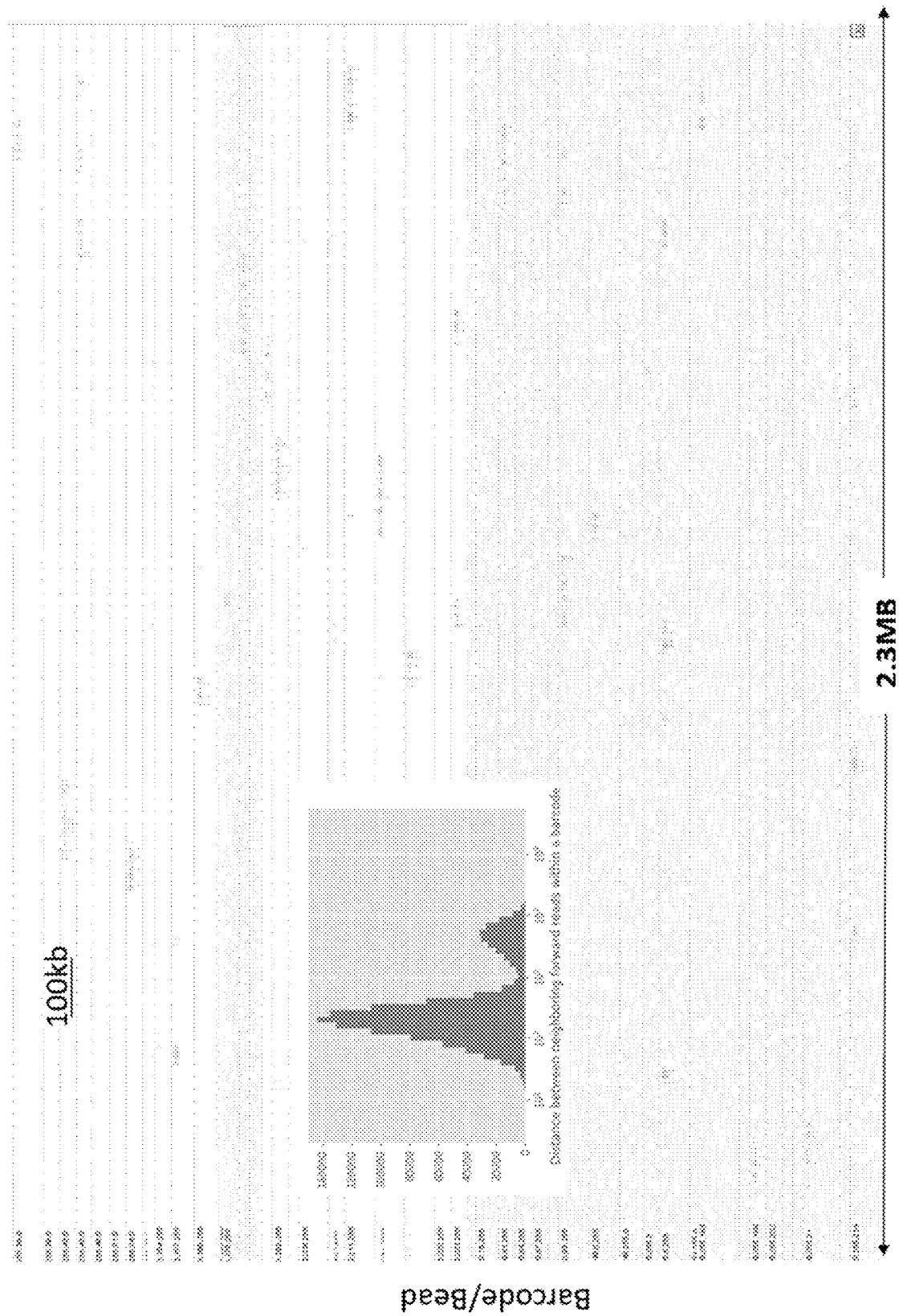

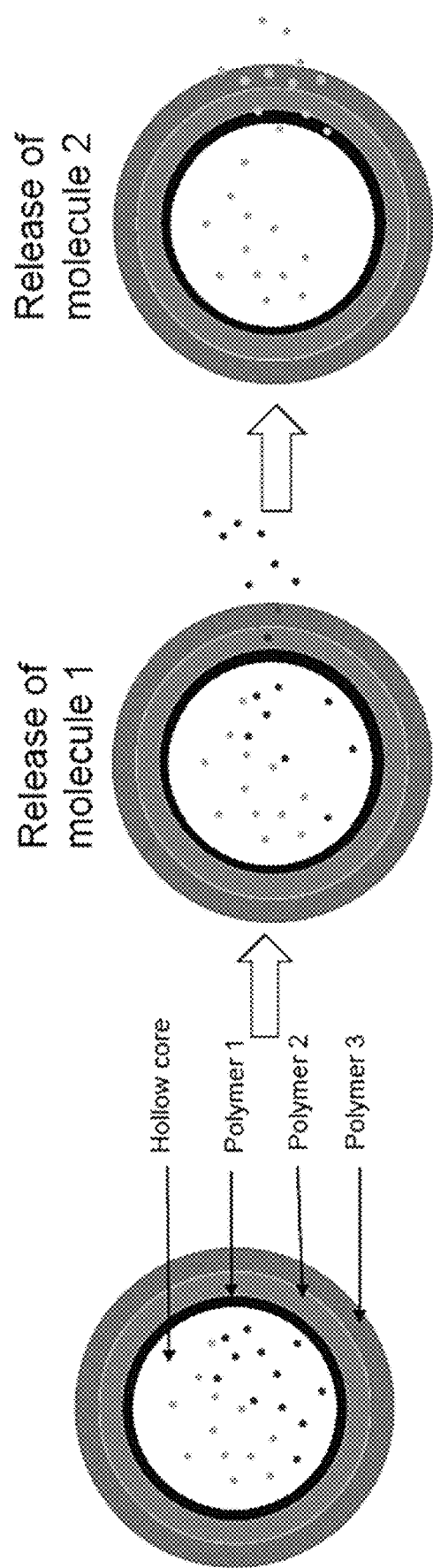

```
SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
aatgatacgg cgaccaccga                                               20

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
caagcagaag acggcatacg a                                             21

<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 3
tttttttttt aatgatacgg cgaccaccga                                    30

<210> SEQ ID NO 4
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 4
tttttttttt caagcagaag acggcatacg a                                  31
```

MODULATING POLYMER BEADS FOR DNA PROCESSING

CROSS-REFERENCE TO RELATED APPLICATIONS

This application is a continuation application of U.S. patent application Ser. No. 16/663,060, filed on Oct. 24, 2019, which claims priority to U.S. Provisional Application No. 62/704,028, filed on Oct. 26, 2018, each of which is hereby incorporated by reference in its entirety.

REFERENCE TO SEQUENCE LISTING

The present application is being filed along with a Sequence Listing in electronic format. The information in the electronic format of the Sequence Listing is incorporated herein by reference in its entirety.

FIELD

Systems, methods, and compositions provided herein relate to polymer beads, methods of encapsulating biomolecules within the polymer beads, and methods of using the polymer beads for conducting assays on the encapsulated biomolecules, including, for example, spatial index sequencing and nucleic acid library preparation.

BACKGROUND

The detection of specific nucleic acid sequences present in a biological sample has been used, for example, as a method for identifying and classifying microorganisms, diagnosing infectious diseases, detecting and characterizing genetic abnormalities, identifying genetic changes associated with various disorders, such as cancer, studying genetic susceptibility to a disease, or measuring responses to various types of treatments. Detecting nucleic acid sequences on a biological sample requires multiple enzymatic reactions to ultimately determine the nucleic acid sequence or to generate a nucleic acid library.

Performing multiple enzymatic reactions on a single cell is unreliable due to the challenges of confining and accessing intracellular biomolecules within a single cell over multiple assays. Many cell-based assays fail to secure intracellular molecules, resulting in loss of biomolecules during performance of the assay.

SUMMARY

Some embodiments relate to a polymer bead for performing multiple co-assay reactions. In some embodiments, the polymer bead comprises a hydrogel polymer precursor, a crosslinker, and a biomolecule disposed within the polymer bead, wherein the bead comprises pores that allow diffusion of one or more reagents through the bead while retaining the biomolecule. In some embodiments, the bead is a porous hydrogel bead or a porous hollow bead. In some embodiments, the bead comprises multiple polymer layers, wherein each layer has a distinct pore size and pore density. In some embodiments, the pores are modulated in size based on changes in charge, pH, or temperature.

Some embodiments relate to a method of performing multiple sequential co-assays on a biomolecule encapsulated within a polymer bead. In some embodiments, the method includes obtaining a polymer bead encapsulating a biomolecule, wherein the polymer bead comprises a hydrogel polymer precursor, a crosslinker, and a biomolecule disposed within the polymer bead, wherein the bead comprises pores that allow diffusion of one or more reagents through the bead while retaining the biomolecule. In some embodiments, the method further includes sequentially contacting the single cell with reagents to perform multiple sequential co-assays. In some embodiments, the method further comprises modulating the size of pores of the polymer bead by adjusting the charge, pH, or temperature. In some embodiments, the polymer bead comprises multiple polymer layers, and each polymer layer has pores of distinct sizes. In some embodiments, the pore size of each polymer layer is specifically modulated by changing the charge, pH, or temperature. In some embodiments, the multiple sequential co-assays include lysis, DNA analysis, RNA analysis, protein analysis, tagmentation, nucleic acid amplification, nucleic acid sequencing, DNA library preparation, assay for transposase accessible chromatic using sequencing (ATAC-seq), contiguity-preserving transposition (CPT-seq), single cell combinatorial indexed sequencing (SCI-seq), or single cell genome amplification, or any combination thereof performed sequentially.

BRIEF DESCRIPTION OF THE DRAWINGS

FIG. 7A shows the spatial reads for cells encapsulated within a polymer bead, and the inset depicts a micrograph showing a cell within the polymer bead. FIG. 7B shows the spatial reads for long DNA fragments encapsulated within a polymer bead, and the inset depicts a micrograph showing the fragments encapsulated within the beads.

FIG. 9 illustrates a graph showing the distribution of barcode reads for long DNA encapsulating within polymer beads.

FIG. 15 illustrates a schematic showing a multilayer polymer bead with each layer having different pore sizes, and the pore sizes of each layer may be separately modulated based on changes in environmental conditions.

FIG. 16A schematically depicts the structure of the polymer bead, which has a shell of N,N'-(1,2-dihydroxyethylene)bisacrylamide (DHEBA) plus acrylate-PEG and potassium peroxydisulfate (KPS). The core is a filler core, such as PEG or polyacrylamide, mixed with sample (cell or DNA). FIG. 16B depicts the formation of the shell around a bead. FIG. 16C shows photomicrographs of the DHEBA shells with sacrificial polyacrylamide cores.

FIG. 17A schematically depicts the structure of the DHEBA shell with an agarose core mixed with sample (cell or DNA). FIG. 17B shows micrographs of the DHEBA shells with agarose cores. FIG. 17C shows micrographs of temperature melting of DHEBA shells having agarose cores.

As shown in FIG. 18A, live cells are contacted with a gelation initiation substance, FITC-AETC. The FITC-AETC coated cells are subjected to radiation and monomers, which forms gel beads around the cells. FIG. 18B depicts micrographs, including excitation microscopy of FITC-AETC treated cells, compared to control cells not treated with FITC-AETC. FIG. 18C shows micrographs of FITC-initiated gelation of cells under various conditions.

DETAILED DESCRIPTION

Figure 1A:
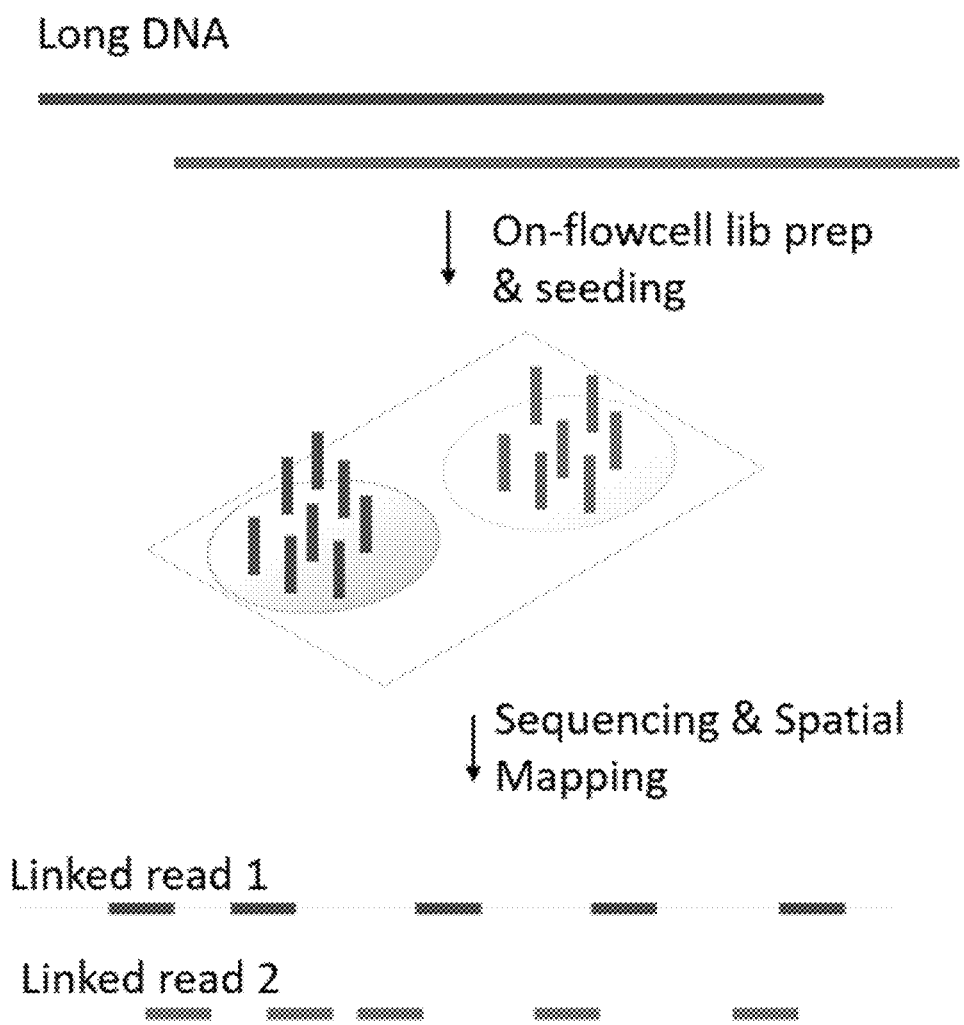
FIG. 1A is a schematic that illustrates an embodiment for spatial indexing of long DNA by on-flow cell library preparation and seeding.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Embodiments relate to compositions, systems, and methods for encapsulating biomolecules within a polymer bead, and performing one or more assay on the encapsulated biomolecules. The polymer bead retains the biomolecules within the bead, but allows diffusion of smaller molecules, such as reagents, into and out of the polymer bead while retaining the biomolecule that is being analyzed. As disclosed herein, the polymer bead includes pores, and the size and density of the pores is modulated to control the size or molecules that diffuse into or out of the polymer beads.

In one embodiment, the polymer bead is a uniform porous hydrogel matrix encapsulating or containing one or more biomolecules. In another embodiment, the polymer bead is a hollow bead having a porous hydrogel shell and a hollow interior, with the biomolecule encapsulated within the hollow interior. In some embodiments, the polymer bead, whether a uniform porous hydrogel matrix or a hollow bead, may include multiple polymer layers, wherein each polymer layer is a distinct matrix having distinct properties, such as pore size. In some embodiments, each polymer layer is controllably modulated to adjust the size of the pore of each polymer layer, thereby allowing a user to control the diffusion of molecules into and out of a polymer bead in a controllable step-wise fashion. In some embodiments, each polymer layer is controllably modulated by changing environmental conditions, such as pH, charge, or temperature, whereby changes in the environmental conditions modulate the pore size of the bead or bead shell, and thereby allow release from or entry into the bead by molecules or reagents in a controllable and step-wise fashion.

The embodiments described herein include reliable and high-throughput systems and methods of performing sequential reactions on a biomolecule encapsulated into a polymer bead. The methods and systems described herein relate to performing one or more assays on the encapsulated biomolecule, including, for example, lysis, DNA analysis, RNA analysis, protein analysis, tagmentation, nucleic acid amplification, nucleic acid sequencing, DNA library preparation, assay for transposase accessible chromatic using sequencing (ATAC-seq), contiguity-preserving transposition (CPT-seq), single cell combinatorial indexed sequencing (SCI-seq), or single cell genome amplification, or any combination thereof performed sequentially.

One embodiment is a method of encapsulating a biomolecule within a polymer bead, loading the polymer beads encapsulating the biomolecule on a flow cell device, preparing a nucleic acid library, releasing the prepared library on a surface of the flow cell device, and clustering and sequencing the released library. In some embodiments, the biomolecule is a cell, a protein, a nucleic acid, a DNA, an RNA, or any derivative or analogue thereof.

In some embodiments, preparing a library includes tagmentation of DNA isolated within the polymer bead. Tagmentation of the encapsulated DNA cleaves longer DNA sequences into shorter tagmentation fragments, which are then used to generate clusters of DNA on a surface of the flowcell. A cluster is a product of a tagmentation fragment of the long DNA, each of which can be sequenced using SBS sequencing, for example. A group of clusters from a single long DNA molecule is referred to herein as a "long DNA island". In some embodiments, a single polymer bead may encapsulate a single long DNA molecule or multiple long DNA molecules. Each long DNA molecule generates a single long DNA island. The clusters of all long DNA islands within a single polymer bead is referred to herein as a "cluster cloud". Thus, a cluster cloud represents all clusters within a single polymer bead, and may include many long DNA islands (each long DNA island representing a single long DNA molecule), and each long DNA island includes multiple clusters.

The beads may include hydrogel polymers and cross-linkers that are mixed in the presence of a biomolecule, such as a nucleic acid such as a long DNA molecule, or a source containing a nucleic acid, which then form polymer beads encapsulating the biomolecule. In some embodiments, the nucleic acid source is a cell.

In some embodiments, the bead pores allow diffusion of a molecule that is less than 1000 base pairs, for example, a molecule that is less than 100, 200, 300, 400, 500, 600, 700, 800, 900, or 1000 base pairs or less, or an amount within a range defined by any two of the aforementioned values, but retains compounds (or does not allow diffusion of compounds) that are greater than the aforementioned values. Thus, in some embodiments, the polymer beads retain (or do not allow diffusion of compounds) greater than 100, 200, 300, 400, 500, 600, 700, 800, 900, 1000, 1500, 2000, 3000, 4000, or 5000 base pairs, or greater, or an amount within a range defined by any two of the aforementioned values.

Some embodiments include methods of using the beads encapsulating a biomolecule to perform nucleic acid reactions, including for example, high-throughput spatial indexing of long DNA molecules. As shown in FIG. 1A, library preparation from a long DNA molecule may be readily prepared by clustering and seeding the clusters from a single long DNA molecule as a "cluster patch" on the surface, which can then be read and spatially mapped. As used herein, the term "long DNA" can include DNA fragments that are greater than 300 base pairs. Long DNA fragments, as used herein, refers to DNA of a length of great than 1 kb, 2.5 kb, 5 kb, or more, such as 10, 15, 20, 25, 30, 35, 40, 45, 50, 60, 70, 80, 90, 100, 200, 300, 400, or 500 kb, or more, including an amount within a range defined by any two of the aforementioned values.

Some embodiments include methods of using a single bead to fragment a genomic sample into a series of long DNA fragments. That single bead can then be adhered to one specific location on a flow cell where the long DNA fragments are deposited such that each of the long DNA fragments are positioned adjacent one another on a flow cell surface. The flow cell may they be used within a nucleotide sequencing system, such as an ILLUMINA HISEQ system to determine the nucleotide sequence from each long DNA fragment. Since the DNA fragments are disposed adjacent one another on the flow cell surface, the system may use this spatial location data to more efficiently reconstruct the final nucleotide sequence of the original genomic DNA. The system may deposit spatially co-located reads directly from single cells, long DNA fragments, or chromosomes. In some embodiments, the methods allow for low input, PCR-free workflow for library preparation. In some embodiments, the methods may be performed without a need for molecular barcoding.

Some embodiments relate to methods of preparing a polymer bead that encapsulates a biomolecule. In some embodiments, the polymer bead encapsulating long DNA can be used to process the cellular genome and perform DNA library preparation inside the bead. In some embodiments, the polymer bead encapsulating a long DNA fragment encapsulates a single cell, which can be used to process the cellular genomic DNA, and to perform whole DNA library preparation inside the bead.

In some embodiments, the pore size of the polymer bead can be engineered to allow the diffusion of enzymes, chemicals, and smaller sized primers (<50 bps), while retaining larger nucleic acids (>300 bps) such that the long DNA fragments and the produced DNA library may be retained inside the polymer beads during processing. In some embodiments, specific primers can be chemically linked within the polymer bead matrix to hybridize and process specific genomic DNA. The DNA library from a single cell can then be released to a specific area, for example, on flow cell surface for library seeding. Subsequently, this results in a spatial distribution of "DNA clusters" on the flow cell originating from the encapsulated long DNA fragments, thus simplifying the read alignment during post processing.

As used herein, the term polymer bead refers to a porous hydrogel bead or a porous hollow bead. In some embodiments, the polymer bead is prepared as a porous hydrogel bead. A porous hydrogel bead is a bead that has a porous matrix of relative uniformity throughout the entire bead. As described herein a porous hydrogel bead encapsulates a biomolecule, and includes pores that allow diffusion of molecules into or out of the porous hydrogel bead. The pores may also be modulated to change the size of the pores based on a change in environmental conditions, such as pH, temperature, or charge, thereby allowing diffusion of molecules into or out of the porous hydrogel beads in a controllable fashion. In some embodiments, a porous hydrogel bead may include one or more types of polymers, each polymer having a distinct pore size and pore density, and each polymer being separately modulated to allow diffusion of different sized molecules based on a change in environmental conditions.

In some embodiments, the polymer bead is prepared as a porous hollow bead. A porous hollow bead is a bead that has a porous polymer shell, but has a hollow interior. As described herein a porous hollow bead encapsulates a biomolecule within the hollow interior. The pores of the polymer shell allow diffusion of molecules into or out of the hollow interior, and can be modulated to change the size of the pores based on a change in the environmental conditions, such as pH, temperature, or charge, thereby allowing diffusion of molecules into or out of the hollow interior in a controllable fashion. In some embodiments, a porous hollow bead includes multiple porous polymer shells, each shell having a distinct pore size and pore density, and each shell being separately modulated to allow diffusion of different sized molecules based on a change in environmental conditions. For example, as shown in FIG. 15, a porous hollow bead may have a hollow interior (or hollow core) with multiple polymer shells. FIG. 15 depicts a porous hollow bead having three porous polymer shells, referred to in FIG. 15 as Polymer 1, Polymer 2, and Polymer 3. Molecules are retained within the porous hollow bead, and modulation of a first polymer results in diffusion of a first molecule through the polymer shell. Modulation of a second polymer results in diffusion of a second molecule through the polymer shell. One of skill in the art will recognize that the example depicted in FIG. 15 is exemplary, and that multiple porous polymer shells may be used for controlling diffusion of molecules into or out of the porous hollow bead. For example, a porous hollow bead may include 1, 2, 3, 4, 5, 6, 7, 8, 9, 10, or more distinct polymer shells, each polymer shell having a specific pore size and pore density, and each polymer shell capable of being modulated to control the diffusion of a molecule into or out of the porous hollow bead.

As used herein, the term "reagent" describes an agent or a mixture of two or more agents useful for reacting with, interacting with, diluting, or adding to a sample, and may include agents used in nucleic acid reactions, including, for example buffers, chemicals, enzymes, polymerase, primers having a size of less than 50 base pairs, template nucleic acids, nucleotides, labels, dyes, or nucleases. In some embodiments, the reagent includes lysozyme, proteinase K, random hexamers, polymerase (for example, (D29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations.

Polymer Beads Encapsulating Biomolecules

One embodiment includes a bead including a hydrogel polymer and a biomolecule. As used herein, the term "hydrogel" refers to a substance formed when an organic polymer (natural or synthetic) is cross-linked via covalent, ionic, or hydrogen bonds to create a three-dimensional open-lattice structure that entraps water molecules to form a gel. In some embodiments, the hydrogel may be a biocompatible hydrogel. As used herein, the term "biocompatible hydrogel" refers to a polymer that forms a gel that is not toxic to living cells and allows sufficient diffusion of oxygen and nutrients to entrapped cells to maintain viability. In some embodiments, the hydrogel polymer includes 60-90% fluid, such as water, and 10-30% polymer. In certain embodiments, the water content of hydrogel is about 70-80%.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO-PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, maleimide (MAL), PEG/MAL, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), PEG/polypropylene oxide (PPO), or N,N'-(1,2-dihydroxyethylene)bisacrylamide (DHEBA).

In some embodiments, a crosslinker forms a disulfide bond in the hydrogel polymer, thereby linking hydrogel polymers. In some embodiments, the hydrogel polymers form a hydrogel matrix or a polymer shell having pores. The pores are capable of retaining sufficiently large molecules within the polymer bead, for example, long DNA fragments, but allow small materials, such as reagents, to pass through the pores, thereby passing in and out of the polymer beads. In some embodiments, the pore size is finely tuned by varying the ratio of the concentration of polymer to the concentration of crosslinker. In some embodiments, the ratio of polymer to crosslinker is 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, or 1:30, or a ratio within a range defined by any two of the aforementioned ratios. In some embodiments, additional functions such as DNA primer, or charged chemical groups can be grafted to polymer matrix to meet the requirements of different applications.

Furthermore, in some embodiments, the pores can be modulated, adjusted, varied, modified, adapted, or tailored in size or density by changing the environmental conditions in which the polymer beads are located, including by changing the pH, the charge, or the temperature. Adjusting the pores can be done in a controllable fashion by making incremental changes to the environment, thereby allowing diffusion of molecules in a controllable manner.

As used herein, the term "porosity" means the fractional volume (dimension-less) of a hydrogel that is composed of open space, for example, pores or other openings. Therefore, porosity measures void spaces in a material and is a fraction of volume of voids over the total volume, as a percentage between 0 and 100% (or between 0 and 1). Porosity of the hydrogel may range from 0.5 to 0.99, from about 0.75 to about 0.99, or from about 0.8 to about 0.95.

The hydrogels can have any pore size. As used herein, the term "pore size" refers to a diameter or an effective diameter of a cross-section of the pores. The term "pore size" can also refer to an average diameter or an average effective diameter of a cross-section of the pores, based on the measurements of a plurality of pores. The effective diameter of a cross-section that is not circular equals the diameter of a circular cross-section that has the same cross-sectional area as that of the non-circular cross-section. In some embodiments, the hydrogel can be swollen when the hydrogel is hydrated. The sizes of the pores size can then change depending on the water content in the hydrogel. In some embodiments, the pores of the hydrogel can have a pore of sufficient size to retain biomolecules within the polymer bead but allow reagents to pass through, and may be adjusted as described herein to allow molecules to pass through in a controllable manner.

In some embodiments, the crosslinker is a reversible crosslinker. In some embodiments, a reversible crosslinker is capable of reversibly crosslinking the hydrogel polymer and is capable of being un-crosslinked in the presence of a cleaver. In some embodiments, a crosslinker can be cleaved by the presence of a reducing agent, by elevated temperature, or by an electric field. In some embodiments, the reversible crosslinker may be N,N'-bis(acryloyl)cystamine, a reversible crosslinker for polyacrylamide gels, wherein a disulfide linkage may be broken in the presence of a suitable reducing agent. In some embodiments, contacting the crosslinker with a reducing agent cleaves the disulfide bonds of the crosslinker, breaking down the polymer beads. The polymer beads degrade, and release the contents, such as nucleic acids that were retained therein. In some embodiments, the crosslinker is cleaved by increasing the temperature to greater than 50, 55, 60, 65, 70, 75, 80, 85, 90, 95, or 100° C. In some embodiments, the crosslinker is cleaved by contacting the polymer beads with a reducing agent. In some embodiments, the reducing agents include phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or β-mercaptoethanol (BME), 2-mercaptoethanol or aminoethanethiol, glutathione, thioglycolate or thioglycolic acid, 2,3-dimercaptopropanol, tris(2-carboxyethyl)phosphine (TCEP), tris(hydroxymethyl)phosphine (THP), or P-[tris(hydroxymethyl)phosphine] propionic acid (THPP).

In some embodiments, elevating the temperature to increase diffusion or contacting with a reducing agent degrades the crosslinker, thereby releasing encapsulated a biomolecule or a molecule derived therefrom from the polymer bead.

Figure 1B:
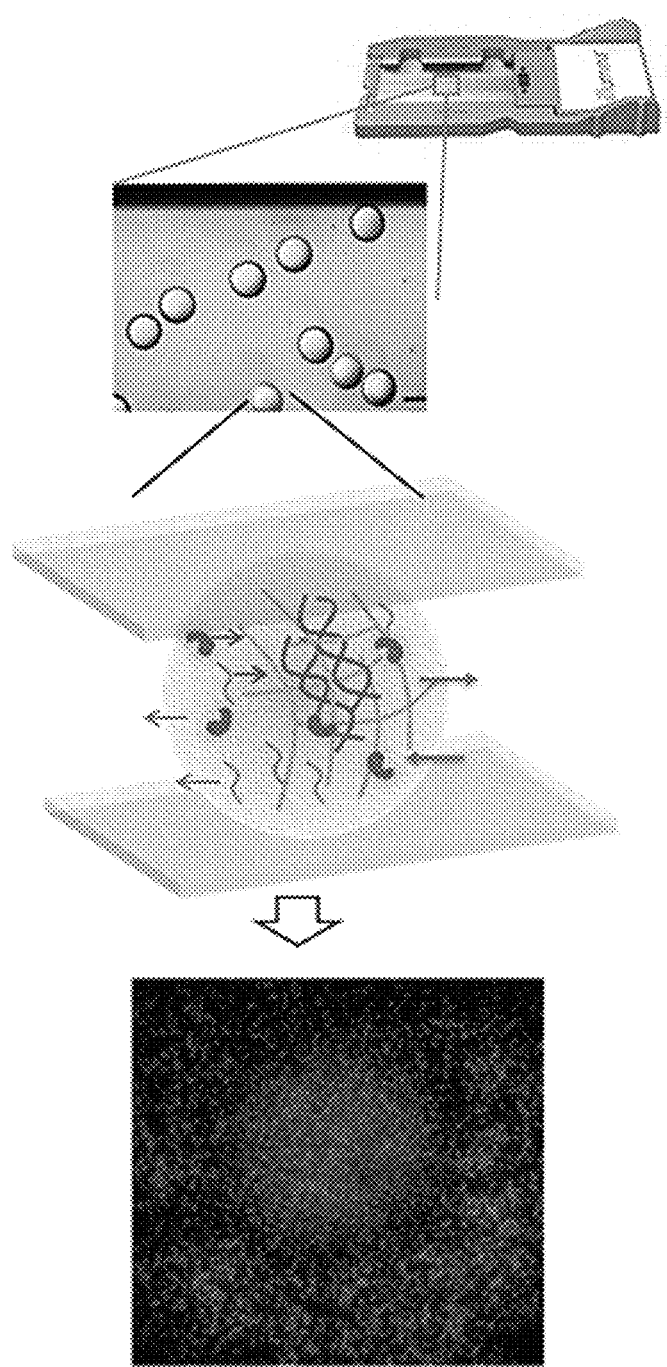
FIG. 1B is a schematic that illustrates spatial indexing using polymer beads that encapsulate long DNA molecules. Reagents may be used on the polymer beads to spatially generate a library on a flow cell surface.

In some embodiments, the crosslinking of the crosslinker establishes pores within the polymer bead. In some embodiments, the size of the pores in the polymer beads are regulatable and are formulated to encapsulate biomolecules, such as DNA fragments of greater than about 5000 base pairs, but to allow smaller particles, such as reagents, or smaller sized nucleic acids of less than about 50 base pairs, such as primers, to pass through the pores, as shown in FIG. 1B. In some embodiments, the reagents including reagents for processing biomolecules or a molecule derived therefrom, such as reagents for isolating nucleic acids from a cell, for amplifying, barcoding, or sequencing nucleic acids, or for preparation of nucleic acid libraries. In some embodiments, reagents include, for example, lysozyme, proteinase K, random hexamers, polymerase (for example, (D29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations.

Figure 7A:
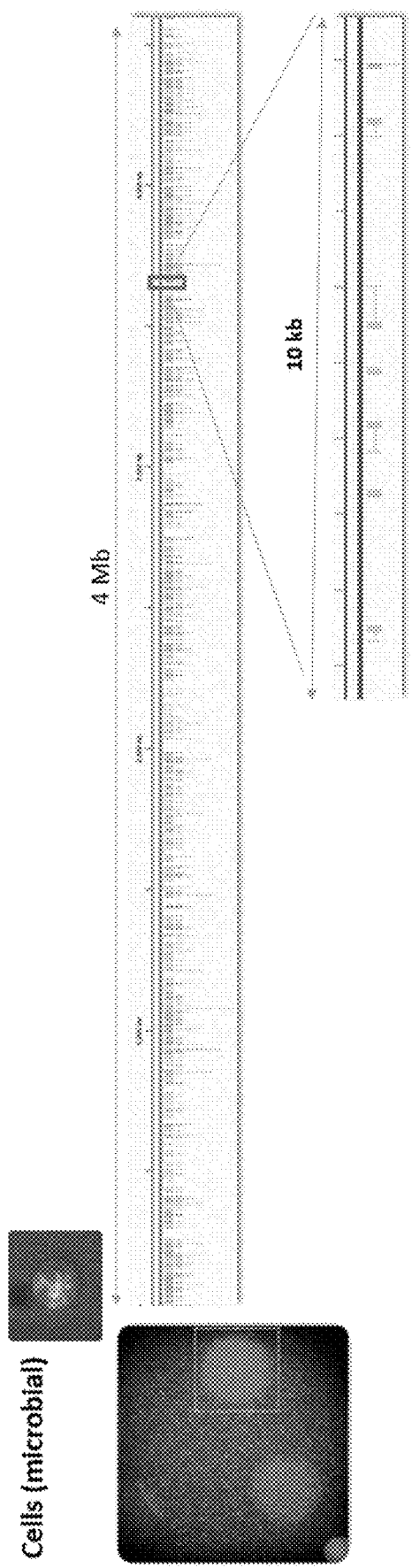
FIGS. 7A and 7B depict line graphs of spatial reads for long DNA encapsulated within a polymer bead.
Figure 7B:
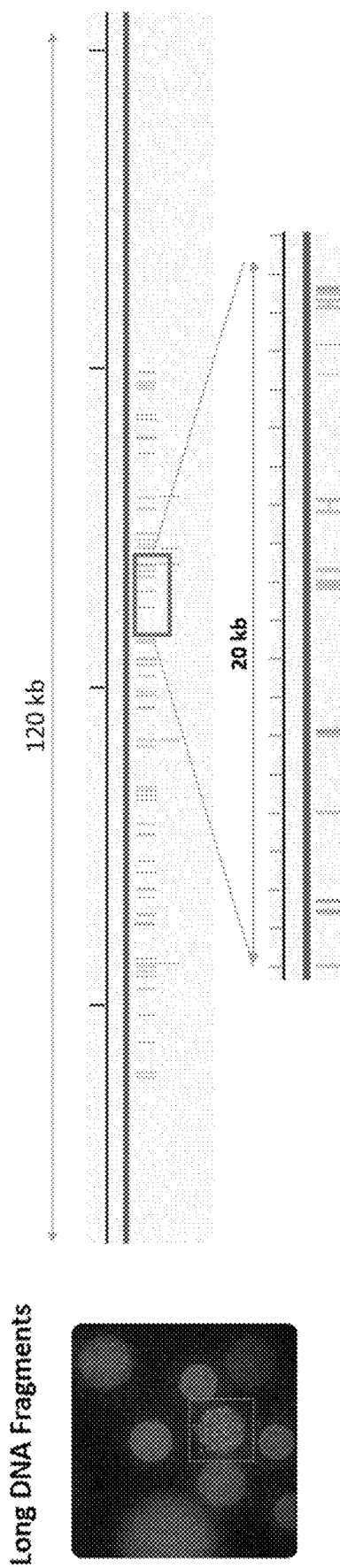
Figure 8:
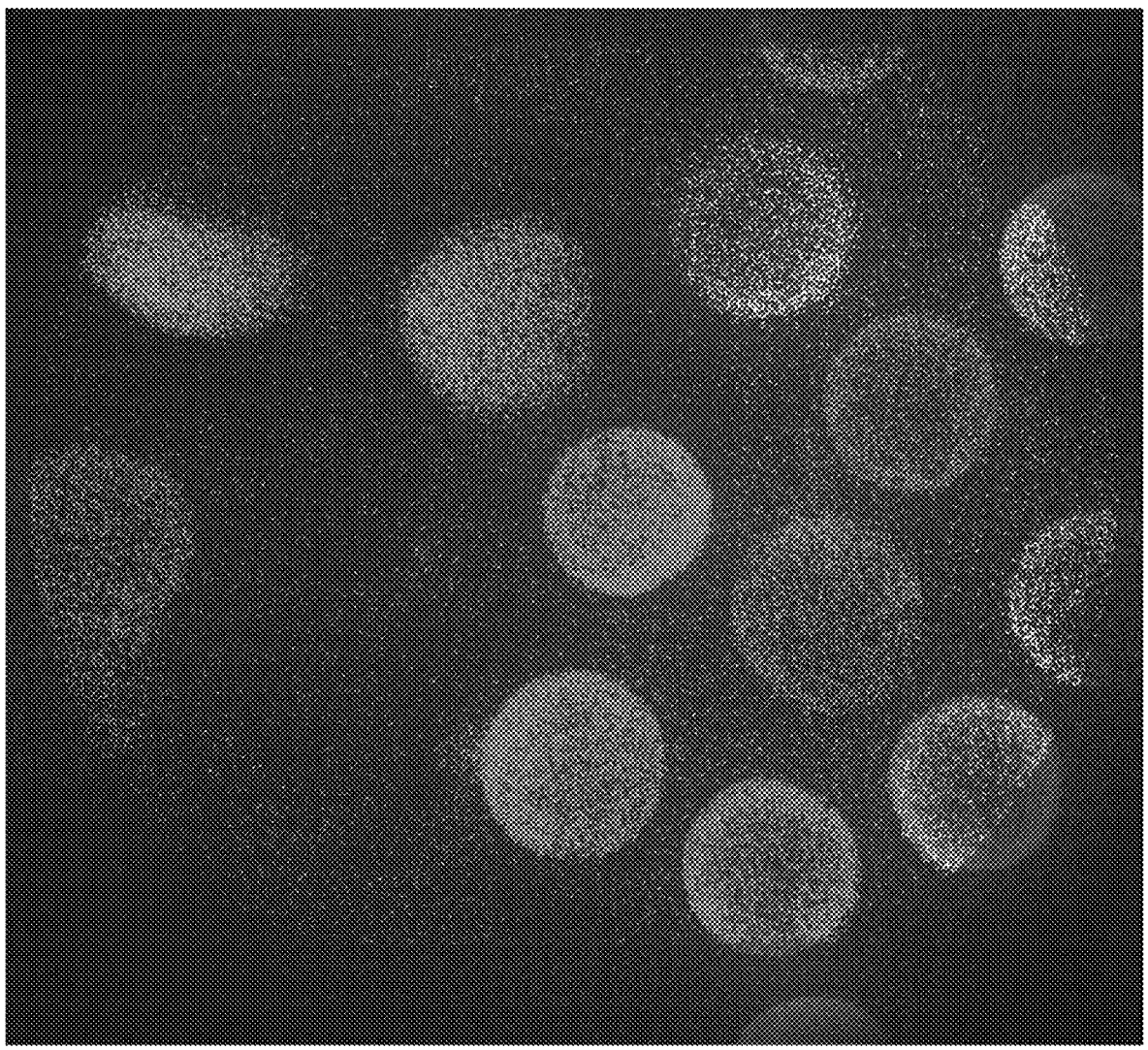
FIG. 8 depicts a micrograph showing identification of microbial species encapsulated within a polymer bead. The polymer bead encapsulated various microbial species, and spatial sequencing reads were performed to identify the microbes.
Figure 10A:
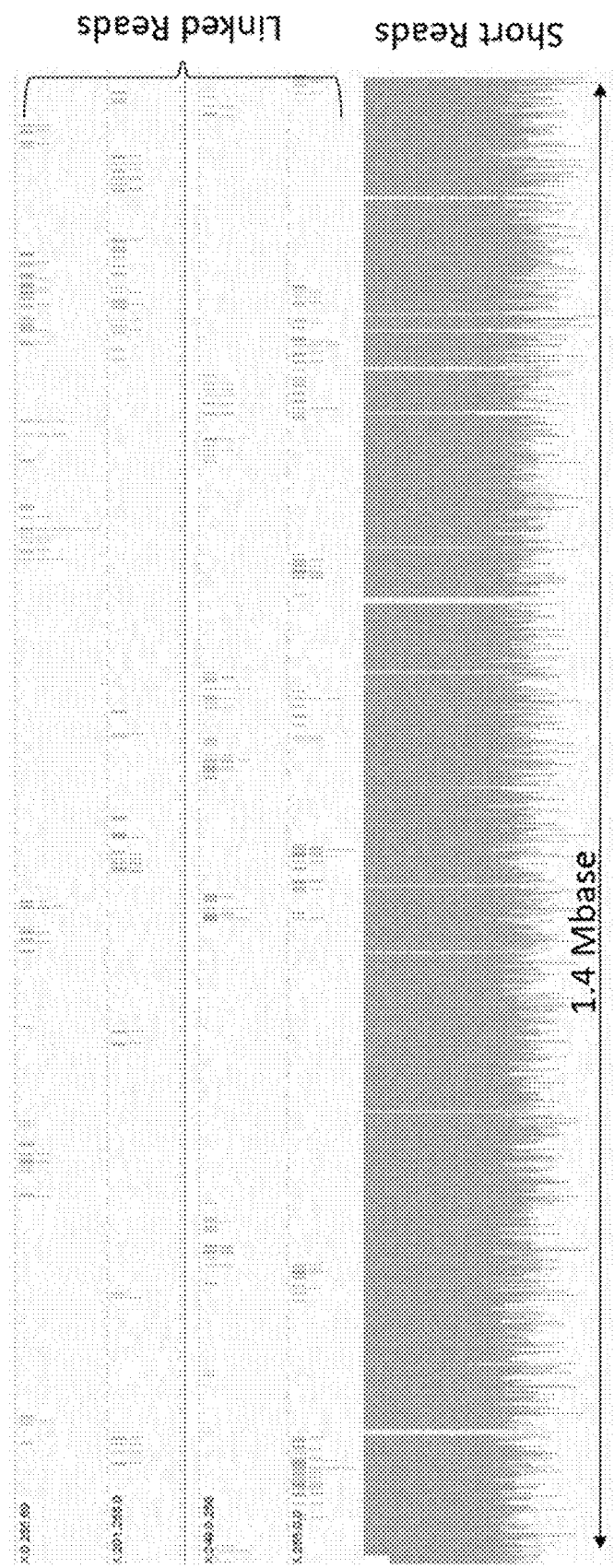
FIG. 10A illustrates a graph showing short reads and linked reads from a single run for an *E. coli* cell encapsulated within a polymer bead. As shown in the figure, linked reads span across repeat regions, and can improve de novo sequence assembly.
Figure 10B:
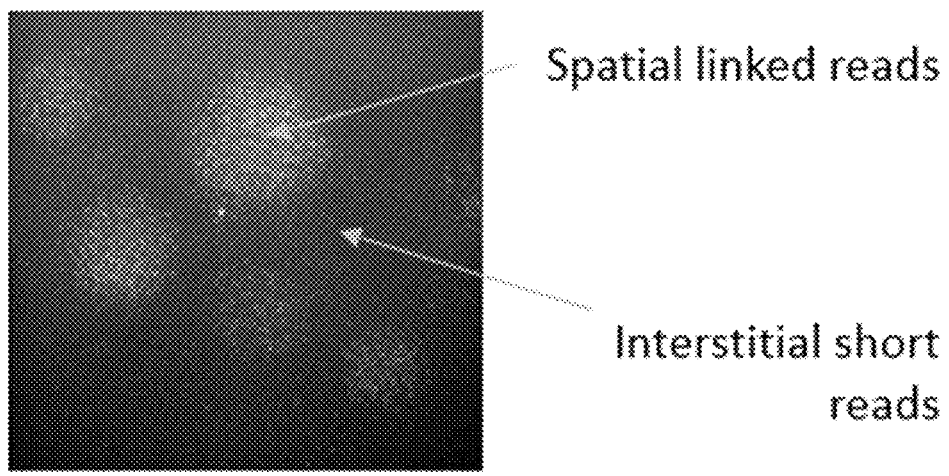
FIG. 10B shows a micrograph depicting spatial linked reads and interstitial short reads.

In some embodiments, the long DNA includes genomic DNA, viral nucleic acids, bacterial nucleic acids, or mammalian nucleic acids. In some embodiments, the polymer beads include a source of long DNA, including, for example a cell. In some embodiments, the cell is a single cell, including a prokaryotic or a eukaryotic cell. In some embodiments, the cell is a mammalian cell. In some embodiments, the cell is a human cell. In some embodiments, the cell is a bacterial cell. Thus, as shown in FIGS. 7A and 7B, the method may be performed on long DNA fragments or on cells, either or both of which is encapsulated with a polymer bead.

In some embodiments, the polymer bead is a sacrificial polymer bead, having a sacrificial core encapsulated by a shell. As used herein, the term "sacrificial" has its ordinary meaning as understood in light of the specification, and refers to a bead or a portion of a bead that is used for preparation or assembly of a bead, but that may be dissolved or discarded at a later stage. In some embodiments, a sacrificial polymer bead includes a polymer material, such as agarose or polyacrylamide that is contacted with a sample, such as a cell or DNA, thereby forming a polymer bead. The polymer bead can then be encapsulated with a shell comprised of a different polymer material having different melting characteristics, such as a shell that includes N,N'-(1,2-dihydroxyethylene)bisacrylamide (DHEBA), acylate-PEG, or KPS, or a combination thereof. After encapsulation, the encapsulated polymer bead may be subjected to conditions sufficient to remove the inner bead, leaving a shell. Conditions may include, for example, change in temperature, pH, or the addition of reducing agents.

In yet further embodiments, any of the polymer beads described herein may include a fluorescent material linked to the polymer material. The fluorescent material may include, for example, fluorescein isothiocyanate (FITC), or any other fluorescing compound, which may be bound to the polymer material, such as to acrylate polymers to form a fluorescing polymer material, such as a FITC-acrylate polymer (FITC-AETC). The fluorescent material linked to polymer material may be contacted with a cell, thereby initiating a fluorescent gelation, forming a fluorescent polymer bead surrounding a cell. In some embodiments, the polymer beads having a cell therein may be imaged fluorescently, without the need for staining.

Methods of Making Polymer Beads

Some embodiments provided herein relate to methods of making beads that encapsulate biomolecules. In some embodiments, the polymer bead is a porous hydrogel bead as described herein or a porous hollow bead as described herein.

In some embodiments, a polymer bead is prepared by vortex assisted emulsion. As used herein, vortex assisted emulsion refers to vortexing a hydrogel polymer with long DNA fragments or a source of long DNA fragments in a container, such as in a tube, vial, or reaction vessel. The components can be mixed, for example by manual or mechanical vortexing or shaking. In some embodiments, manual mixing results in polymer beads that encapsulate biomolecules having a size of 2, 3, 4, 5, 10, 15, 20, 25, 30, 35, 40, 45, 50, 55, 60, 65, 70, 75, 80, 85, 90, 95, 100, 110, 120, 130, 140, or 150 µm in diameter, or a size within a range defined by any two of the aforementioned values. In some embodiments, the size of the beads is non-uniform, and thus, the size of the beads includes beads of various diameters.

In some embodiments, the beads are prepared by microfluidic droplet generation. As shown in FIG. 1B, microfluidic droplet generation includes use of a microfluidic device for assisted gel emulsion generation. In some embodiments, the microfluidic device includes microchannels configured to produce a polymer bead of a desired size and configured to encapsulate a selected amount of biomolecule per bead. In some embodiments, the microfluidic device has a height of 50, 60, 70, 80, 90, 100, 110, 120, 130, 140, 150, 160, 170, 180, 190, or 200 µm, or a height within a range defined by any two of the aforementioned values. In some embodiments, the microfluidic device includes one or more channels. In some embodiments, the microfluidic device includes a channel for an aqueous stream and a channel for an immiscible fluid. In some embodiments, the width of the one or more channels is identical. In some embodiments, the width of the one or more channels is different. In some embodiments, the width of the one or more channels is 20, 30, 40, 45, 50, 55, 60, 65, 70, 75, 80, 85, 90, 95, 100, 105, 110, 115, 120, 125, 130, 135, 140, 145, or 150 µm, or a width within a range defined by any two of the aforementioned values. In some embodiments, the width of the aqueous channel is 75 µm. In some embodiments, the width of the immiscible fluid channel is 78 µm. One of skill in the art will recognize that the width can vary to finely tune the size of the bead. In addition to the size of the microfluidic device and the width of the channels, the flow rate of the aqueous channel and the immiscible fluid channel may also affect the size of the polymer beads.

In some embodiments, the flow rate of the solution in the aqueous phase channel is 1, 2, 5, 10, 20, 30, 40, 50, 60, 70, 80, 90, 100, 110, 120, 130, 140, or 150 µL/min, or a rate within a range defined by any two of the aforementioned values. In some embodiments, the flow rate of the immiscible fluid in the immiscible fluid channel is 20, 30, 50, 80, 100, 150, 160, 170, 180, 190, 200, 225, 250, 275, 300, 325, 350, 375, or 400 µL/min, or a rate within a range defined by any two of the aforementioned values. In some embodiments, the solution in the aqueous phase includes a hydrogel polymer, a crosslinker, and a biomolecule, which flows through an aqueous channel into an immiscible fluid, such as a carrier oil, at a flow rate less than the flow rate of the immiscible fluid, thereby forming droplets. In some embodiments, the immiscible fluid is oil, such as mineral oil, a hydrocarbon oil, a silicon oil, a polydimethylsiloxane oil, tetramethylethylenediamine (TEMED), or mixtures thereof. In some embodiments, the hydrogel droplets containing a biomolecule are formulated in a uniform size distribution. In some embodiments, the size of the polymer beads is finely tuned by adjusting the size of the microfluidic device, the size of the one or more channels, or the flow rate of either or both of the aqueous solution or immiscible fluid. In some embodiments, the resulting polymer bead has a diameter ranging from 2 to 150 µm, for example, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, or 150 µm, or a diameter within a range defined by any two of the aforementioned values.

In some embodiments, the size and uniformity of the polymer bead encapsulating a biomolecule can be further controlled by contacting a hydrogel polymer prior to bead formation with a fluidic modifier, such as with an alcohol, including isopropyl alcohol.

In some embodiments, the amount of long DNA fragments encapsulated within a bead can be controlled by diluting or concentrating the long DNA fragments within the inputted sample. The sample including the long DNA fragments is mixed with hydrogel polymer, and the hydrogel polymer containing the long DNA fragments is submitted to vortex assisted emulsion or microfluidic droplet generation, as described herein.

In some embodiments, the polymer beads may be functionalized and used for purification of a nucleic acid. In some embodiments, the polymer beads are functionalized with a nucleotide. In some embodiments, the nucleotide is an oligonucleotide or polyT nucleotide. In some embodiments, the nucleotide is bound to the polymer bead, and the functionalized bead can be used for targeted capture of a nucleotide of interest.

In some embodiments, the polymer bead may be encapsulated with a polymer shell having different characteristics from the polymer bead, such as different melting temperature, different pore sizes, or different dissolution characteristics. In some embodiments, the polymer shell can include a DHEBA material.

Methods of Processing Biomolecules Encapsulated within Polymer Beads

Figure 2:
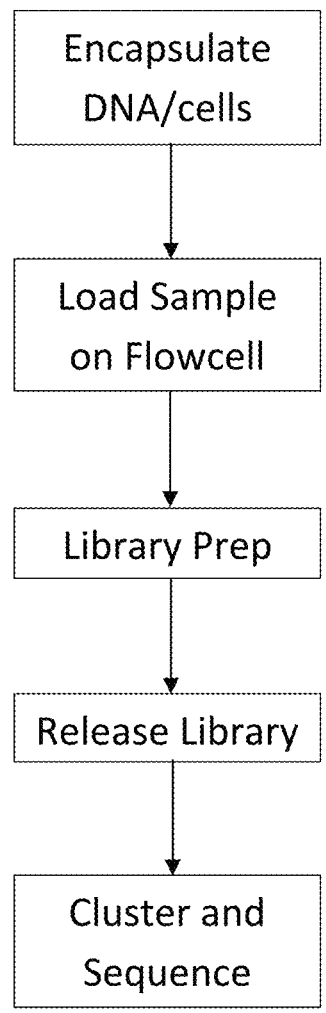
FIG. 2 is a flow diagram that depicts a method of encapsulating long DNA within a polymer bead, and preparing a library within the polymer bead, which can be clustered and sequenced on a flow cell device.
Figure 3:
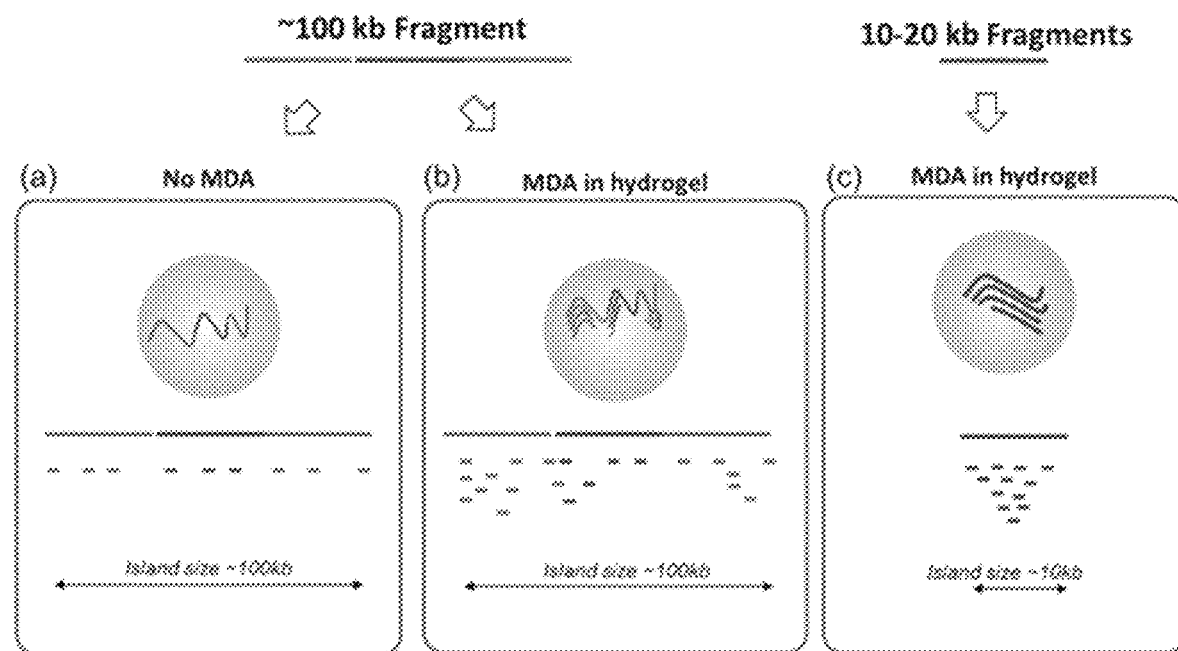
FIG. 3 is a schematic that illustrates workflow of DNA sequencing of long DNA encapsulated within polymer beads, including DNA fragments of about 100 kb (without a multiple displacement amplification (MDA) step (panel (a)) or with an MDA step (panel (b)) prior to tagmentation) and DNA fragments of about 10-20 kb (panel (c)).
Figure 4:
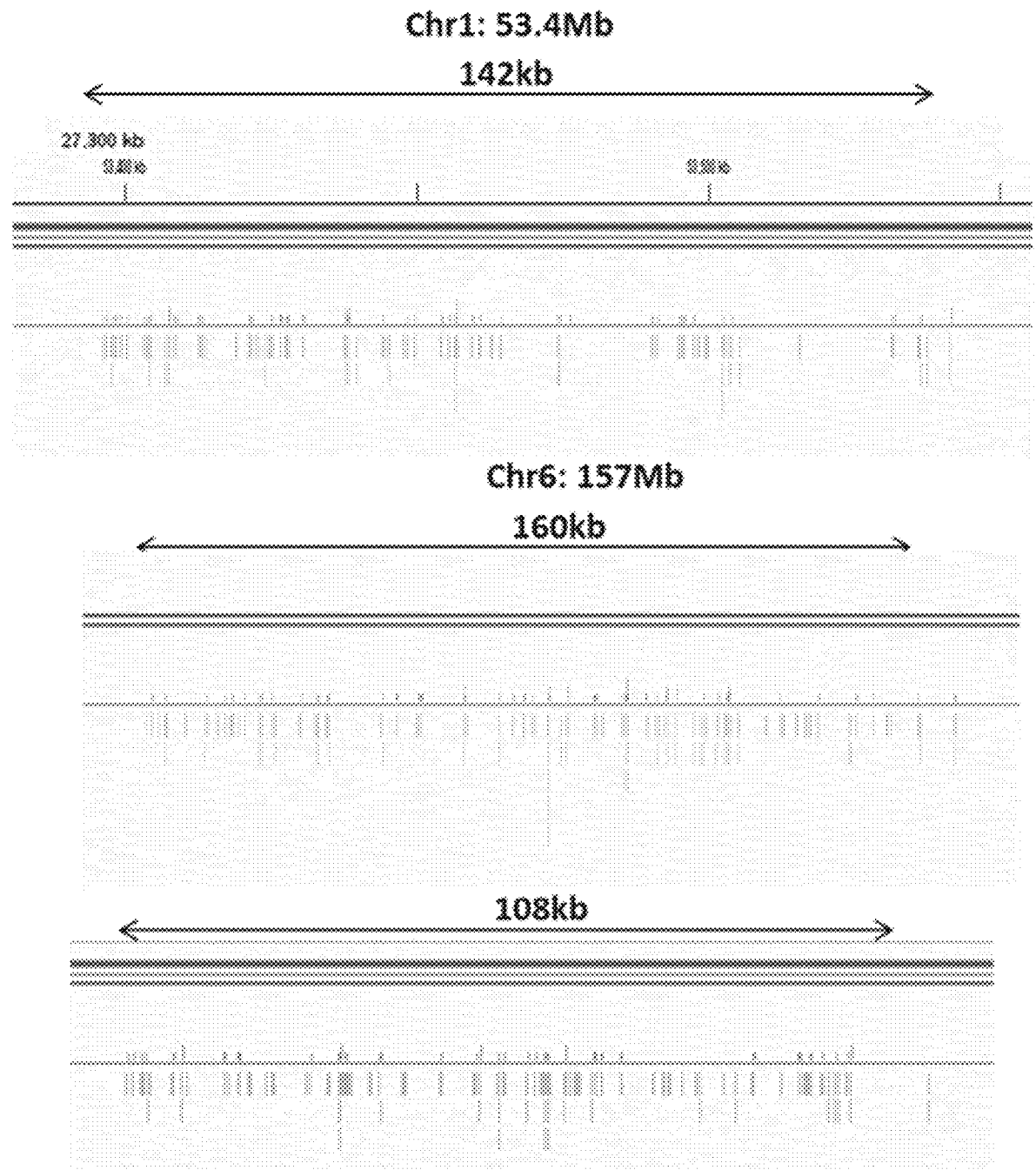
FIG. 4 is a graph that depicts strobed reads of long DNA hydrogel spatial indexing sequencing data from a 100 kb DNA fragment without MDA.

Some embodiments include methods of processing biomolecules within a bead as shown in FIG. 2, which depicts a flow diagram for preparing and processing biomolecules in a polymer bead. In a first step, a DNA sample, such as from genomic data or a cell is encapsulated within a polymer bead. In some embodiments, a long DNA fragment is retained within the polymer beads, and reagents are able to pass through the pores of the polymer beads. In some embodiments, reagents can include lysis agents, nucleic acid purification agents, tagmentation agents, PCR agents, or other agents used in processing of biomolecules or molecules derived therefrom. Thus, the polymer beads provide a microenvironment for controlled reactions of long DNA fragments within the polymer beads by allowing a barrier for reagents to pass in and out of the polymer beads, while retaining the long DNA fragments within the beads. Once the DNA is encapsulated into the beads, the process moves to the next step where the sample can be loaded into a flow cell to create the long DNA fragments through the library preparation process.

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences can be added to the ends of the adapted fragments, for example by PCR, ligation, or any other suitable methodology known to those of skill in the art.

In some embodiments, entire DNA library preparation can be accomplished seamlessly inside the polymer beads bound to the flow cell with multiple reagent exchanges by passing through the porous hydrogel while retaining the gDNA and its library products within the hydrogel matrix. The hydrogel may be resistant to high temperatures up to 95° C. for several hours to support different biochemical reactions.

In the next step in the process, the polymer bead encapsulating the long DNA fragments from the prior library preparation is treated to release, purify and isolate the long DNA fragments from the bead. Thus, for example the polymer bead is contacted with a lysis buffer. As used herein, "lysis" means perturbation or alteration to a cell wall or viral particle facilitating access to or release of the cellular RNA or DNA. Neither complete disruption nor breakage of the cell wall is an essential requirement for lysis. By the term "lysis buffer" is meant a buffer that contains at least one lysing agent. Typical enzymatic lysing agents include, but are not limited to, lysozyme, glucolase, zymolose, lyticase, proteinase K, proteinase E, and viral endolysins and exolysins. Thus, for example, lysis of cells in the beads may be performed by introducing lysing agents, such as lysozyme and proteinase K into the polymer beads. The gDNA from the cells is now contained within the beads. In some embodiments, following lysis treatment, isolated nucleic acid is retained within the polymer bead, and may be used for further processing.

As used herein, the terms "isolated," "to isolate," "isolation," "purified," "to purify," "purification," and grammatical equivalents thereof as used herein, unless specified otherwise, refer to the reduction in the amount of at least one contaminant (such as protein and/or nucleic acid sequence) from a sample or from a source (e.g., a cell) from which the material is isolated. Thus purification results in an "enrichment," for example, an increase in the amount of a desirable protein and/or nucleic acid sequence in the sample.

In some embodiments, the encapsulated nucleic acids are sequenced in full or in part within the polymer beads. The encapsulated nucleic acids can be sequenced according to any suitable sequencing methodology, such as direct sequencing, including sequencing by synthesis, sequencing by ligation, sequencing by hybridization, nanopore sequencing and the like.

Some embodiments provided herein relate to sequencing-by-synthesis (SBS) enabled for long DNA fragments. In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

One or more amplified encapsulated nucleic acids can be subjected to an SBS or other detection technique that involves repeated delivery of reagents in cycles. For example, to initiate a first SBS cycle, one or more labeled nucleotides, DNA polymerase, etc., can be flowed into/ through a polymer bead that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with amplicons produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210, 891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero mode waveguides (ZMWs). Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available. Examples of such sequencing systems are pyrosequencing (e.g. commercially available platform from 454 Life Sciences a subsidiary of Roche), sequencing using γ-phosphate-labeled nucleotides (e.g. commercially available platform from Pacific Biosciences) and sequencing using proton detection (e.g. commercially available platform from Ion Torrent subsidiary of Life Technologies) or sequencing methods and systems described in US 2009/0026082 A1; US 2009/ 0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008), the disclosures of which are incorporated herein by reference).

Exemplary methods for array-based expression and genotyping analysis that can be applied to detection according to the present disclosure are described in U.S. Pat. Nos. 7,582, 420; 6,890,741; 6,913,884 or 6,355,431 or US Pat. Pub. Nos. 2005/0053980 A1; 2009/0186349 A1 or US 2005/0181440 A1, each of which is incorporated herein by reference.

In the methods of isolating nucleic acids, amplification, and sequencing as described herein, various reagents are used for nucleic acid isolation and preparation. Such reagents may include, for example, lysozyme, proteinase K, random hexamers, polymerase (for example, (D29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations. These reagents pass through the pores of the polymer beads, whereas the biomolecule or molecule derived therefrom is retained within the polymer beads. An advantage of the methods set forth herein is that they provide for an encapsulated microenvironment for the processing of nucleic acids within a polymer bead. This enables single cell processing for rapid and efficient processing of a target nucleic acid.

Adaptors can include sequencing primer sites, amplification primer sites, and indexes. As used herein an "index" can include a sequence of nucleotides that can be used as a molecular identifier and/or barcode to tag a nucleic acid, and/or to identify the source of a nucleic acid. In some embodiments, an index can be used to identify a single nucleic acid, or a subpopulation of nucleic acids. In some embodiments, nucleic acid libraries can be prepared within a polymer bead. In some embodiments, a single cell encapsulated within a polymer bead may be used for combinatorial indexing of the single cells, for example, using a contiguity preserving transposition (CPTSeq) approach. In some embodiments, DNA from a single cell may be barcoded by encapsulation of single cells after WGA amplification with another bead carrying barcoded transposons and dissolving the gel matrix by contacting it with a reducing agent, for example, to release genomic DNA for barcoding.

Embodiments of the "spatial indexing" methods and techniques described herein shortens data analysis and simplifies the process of library preparation from single cells and long DNA molecules. Existing protocols for single cell sequencing requires efficient physical separation of the cells and uniquely barcoding each isolated cell and pooling everything back together to do sequencing. Current protocols for synthetic long reads also requires cumbersome barcoding steps, and pooling each barcoded fragments together for sequencing and letting data analysis to distinguish genetic information coming from each barcoded cell. During these processes there may be loss of material which causes dropouts in the sequences. Embodiments described herein not only shorten the process but also increase data resolution for single cells. Furthermore, embodiments provided herein simplify the assembly of genomes of new organisms. Embodiments described herein may be used to reveal rare genetic variations and co-occurrence of mutations. In some embodiments, DNA library confined in the polymer beads until release provide the opportunity to control the size of the fragments that is released on the surface by controlling the release process and hydrogel formulation.

In some embodiments, the surface is a flow cell device. In some embodiments, the flow cell is a custom flow cell device having wells, grooves, or patterns. In some embodiments, the flow cell comprises a patterned surface. In some embodiments, the patterned surface comprises wells. In some embodiments, the wells are from about 10 µm to about 50 µm in diameter, such as 10 µm, 15 µm, 20 µm, 25 µm, 30 µm, 35 µm, 40 µm, 45 µm, or 50 µm in diameter, or within a range defined by any two of the aforementioned values, and wherein the wells are about 0.5 µm to about 1 µm in depth, such as 0.5 µm, 0.6 µm, 0.7 µm, 0.8 µm, 0.9 µm, or 1 µm in depth, or within a range defined by any two of the aforementioned values. In some embodiments, the wells are comprised of hydrophobic material. In some embodiments, the hydrophobic material comprises an amorphous fluoropolymer, such as CYTOP, Fluoropel®, or Teflon®.

In some embodiments, the library may be amplified using primer sites in the adaptor sequences, and sequenced using sequencing primer sites in the adaptor sequences. In some embodiments the adaptor sequences can include indexes to identify the source of the nucleic acids. The efficiency of subsequent amplification steps can be reduced by the formation of primer-dimers. To increase the efficiency of subsequent amplification steps, non-ligated single-stranded adaptors can be removed from ligation products.

Figure 11A:
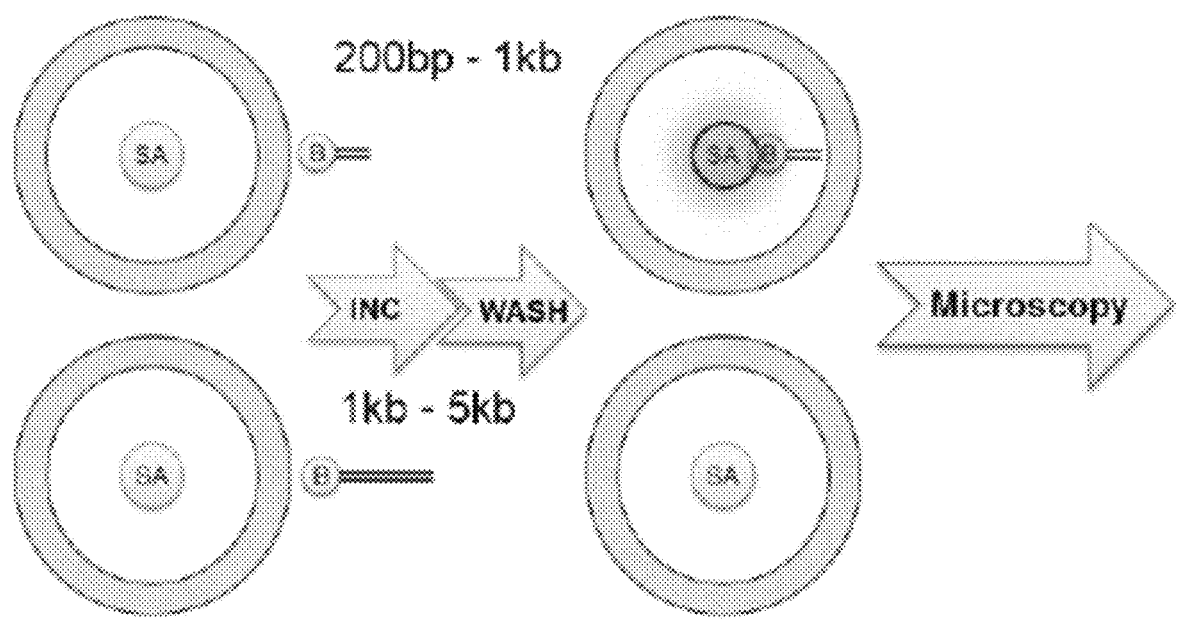
FIG. 11A is a schematic that illustrates diffusion of molecules into a polymer bead based on pore size and pore density.
Figure 11B:
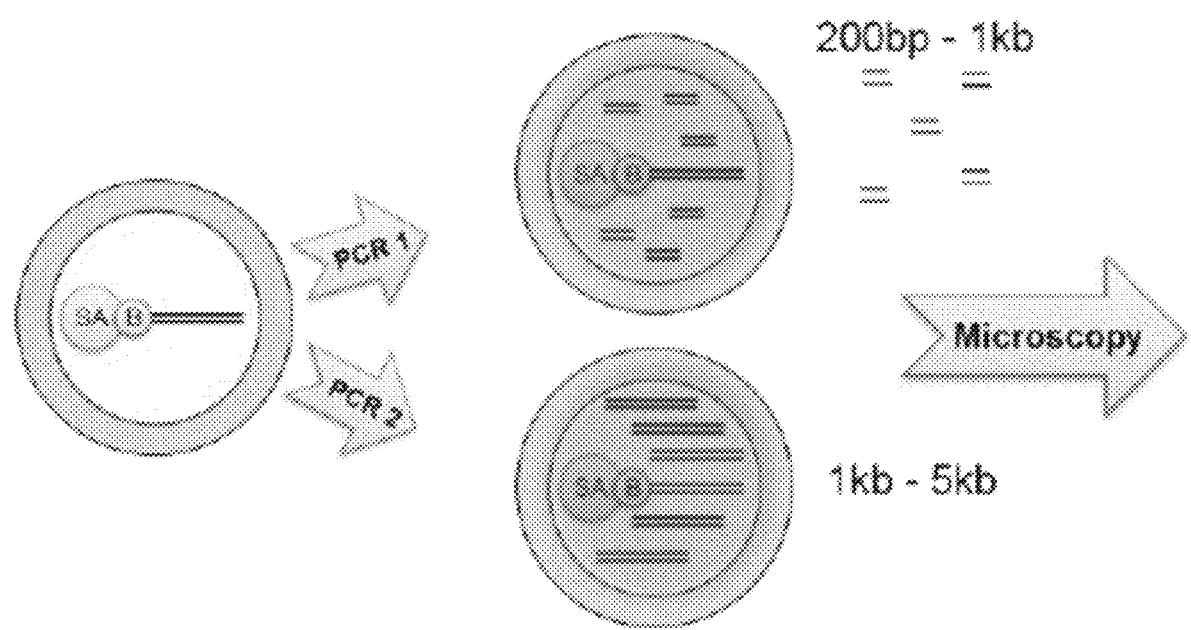
FIG. 11B is a schematic that illustrates diffusion of molecules outside of a polymer bead.

In some embodiments, a model system can be prepared to determine the porosity of the polymer beads. As shown in FIGS. 11A and 11B, a polymer bead may encapsulate a streptavidin compound (depicted in FIGS. 11A and 11B as SA), retaining the streptavidin compound within the bead. In some embodiments, a biotin compound linked to an amplicon of a certain size is mixed with the polymer bead (FIG. 11A). A biotin linked amplicon of sufficient size is capable of diffusing into the polymer bead and conjugating to the streptavidin within the bead, thereby retaining the biotin linked amplicon within the bead. Conversely, biotin linked amplicon that is excessively large will not pass through the polymer bead, and no amplicon is retained within the bead. Similarly, a polymer bead may be prepared having a streptavidin conjugated to a biotin linked amplicon, and reagents may pass through to perform a reaction, such as PCR (FIG. 11B). Fragments that are sufficiently sized diffuse out of the polymer bead, whereas fragments that are excessively large do not diffuse through the polymer bead, and are retained within the bead.

Preparing Nucleic Acid Libraries with Polymer Beads

Some embodiments of the systems, methods and compositions provided herein include methods in which adaptors are ligated to target nucleic acids. Adaptors can include sequencing primer binding sites, amplification primer binding sites, and indexes. For example, an adaptor can include a P5 sequence, a P7 sequence, or a complement thereof. As used herein a P5 sequence comprises a sequence defined by SEQ ID NO: 1 (AATGATACGGCGACCACCGA) and a P7 sequence comprises a sequence defined by SEQ ID NO: 2 (CAAGCAGAAGACGGCATACGA). In some embodiments, the P5 or P7 sequence can further include a spacer polynucleotide, which may be from 1 to 20, such as 1 to 15, or 1 to 10, nucleotides, such as 2, 3, 4, 5, 6, 7, 8, 9, or 10 nucleotides in length. In some embodiments, the spacer includes 10 nucleotides. In some embodiments, the spacer is a polyT spacer, such as a 10T spacer. Spacer nucleotides may be included at the 5' ends of polynucleotides, which may be attached to a suitable support via a linkage with the 5' end of the polynucleotide. Attachment can be achieved through a sulphur-containing nucleophile, such as phosphorothioate, present at the 5' end of the polynucleotide. In some embodiments, the polynucleotide will include a polyT spacer and a 5' phosphorothioate group. Thus, in some embodiments, the P5 sequence is 5'phosphorothioate-TTTTTTTTTTAATGATACGGCGACCACCGA-3' (SEQ ID NO: 3), and in some embodiments, the P7 sequence is 5'phosphorothioate-TTTTTTTTTTCAAGCAGAAGACGGCATACGA-3' (SEQ ID NO: 4).

Indexes can be useful to identify the source of a nucleic acid molecule. In some embodiments, an adaptor can be modified to prevent the formation of concatemers, for example by the addition of blocking groups that prevent extension of the adaptor at one or both ends. Examples of 3' blocking groups include a 3'-spacer C3, a dideoxynucleotide, and attachment to a substrate. Examples of 5' blocking groups include a dephosphorylated 5' nucleotide, and attachment to a substrate.

Adaptors include nucleic acids, such as single-stranded nucleic acids. Adaptors can include short nucleic acids having a length less than, greater than, or equal to about 5 nucleotides, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, or a range between any two of the foregoing sizes. In some embodiments, the adaptors are of sufficient size to pass through the pores of the polymer beads. Target nucleic acids include DNA, such as genomic or cDNA; RNA, such as mRNA, sRNA or rRNA; or a hybrid of DNA and RNA. The nucleic acid can be isolated from a single cell encapsulated within a polymer bead. A nucleic acid can contain phosphodiester bonds, and can include other types of backbones, comprising, for example, phosphoramide, phosphorothioate, phosphorodithioate, O-methylphosphoroamidite and peptide nucleic acid backbones and linkages. A nucleic acid can contain any combination of deoxyribo- and ribonucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole). In some embodiments, a nucleic acid can include at least one promiscuous base. A promiscuous base can base-pair with more than one different type of base and can be useful, for example, when included in oligonucleotide primers or inserts that are used for random hybridization in complex nucleic acid samples such as genomic DNA samples. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole. Promiscuous bases that can base-pair with at least two, three, four or more types of bases can be used.

An example method includes dephosphorylating the 5' ends of target nucleic acids to prevent the formation of concatemers in subsequent ligation steps; ligating first adaptors to the 3' ends of the dephosphorylated targets using a ligase, in which the 3' ends of the first adaptors are blocked; re-phosphorylating of the 5' ends of the ligated targets; ligating a second adaptor to the 5' ends of the dephosphorylated targets using the single-stranded ligase, in which the 5' ends of the second adaptors are non-phosphorylated.

Another example includes partial digestion of the nucleic acid with a 5' exonuclease to form a double-stranded nucleic acid with single-stranded 3' overhangs. An adaptor containing a 3' blocking group can be ligated to the 3' ends of double-stranded nucleic acid with 3' overhangs. The double-stranded nucleic acid with 3' overhangs with ligated adaptors can be dehybridized to form single-stranded nucleic acids. An adaptor containing a non-phosphorylated 5' end can be ligated to the 5' end of the single-stranded nucleic acid.

Methods to dephosphorylate nucleic acids, such as the 5' nucleotide of a nucleic acid include contacting a nucleic acid with a phosphatase. Examples of phosphatases include calf intestinal phosphatase, shrimp alkaline phosphatase, antarctic phosphatase, and APEX alkaline phosphatase (Epicentre).

Methods to ligate nucleic acids include contacting nucleic acids with a ligase. Examples of ligases include T4 RNA ligase 1, T4 RNA ligase 2, RtcB ligase, *Methanobacterium* RNA ligase, and TS2126 RNA ligase (CIRCLIGASE).

Methods to phosphorylate nucleic acids, such as the 5' nucleotide of a nucleic acid include contacting a nucleic acid with a kinase. Examples of kinases include T4 polynucleotide kinase.

Embodiments provided herein relate to preparing nucleic acids libraries in a polymer bead, such that the nucleic acid library is prepared in a single reaction volume.

Embodiments of the systems and methods provided herein include kits, containing any one or more of the hydrogel polymers, crosslinkers, or microfluidic devices for preparing polymer beads that encapsulate biomolecules, and further including components useful for processing of the biomolecules or molecules derived therefrom, including reagents for cell lysis, and nucleic acid amplification and sequencing, or for nucleic acid library preparation, including lysozyme, proteinase K, random hexamers, polymerase (for example, (Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations as described herein, and as used for the respective processing of biomolecules or molecules derived therefrom.

Figure 12:
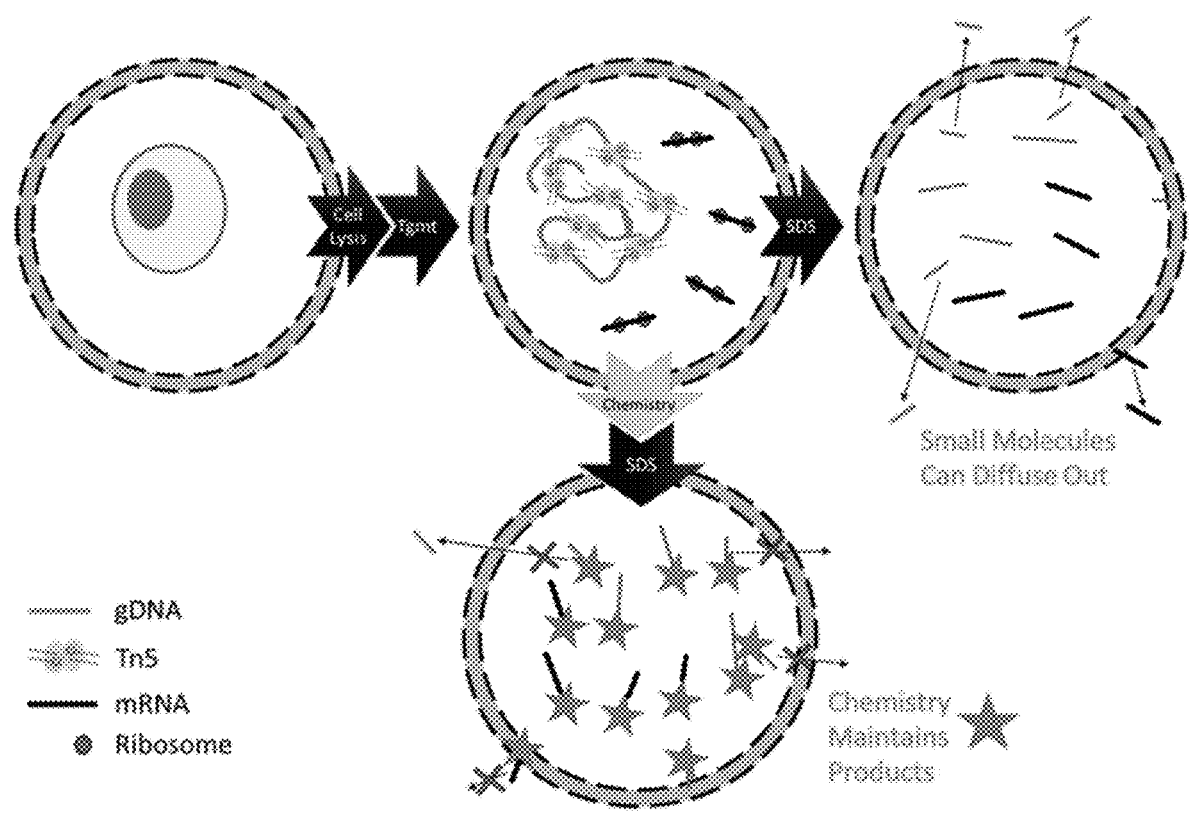
FIG. 12 is a schematic that illustrates retention of nucleic acid libraries within a polymer bead.

As shown in FIG. 12, a polymer bead is prepared encapsulating a cell. The polymer bead is exposed to reagents for cell lysis and tagmentation. Treatment of the polymer bead with a detergent, such as SDS, results in fragmentation and small molecules can diffuse out of the polymer bead. In some embodiments, retainability of cellular biomolecules can be limited by a minimum threshold limit beyond which two-way access of enzymes into the Cells would be restricted.

Alternatively, in some embodiments, library preparation methods are performed to increase the physical size of genomic molecules so they are contained within the polymer beads, which overcome the threshold limit. Thus, as shown in FIG. 12, during gDNA library preparation, tagmented gDNA fragments are held together by Tn5 binding, preventing diffusion outside of polymer beads. However, after SDS treatment, Tn5 is released and the resulting library fragments may diffuse out if too small. To prevent this, a Tn5 enzyme with overhanging transposon ends may be used for tagmentation. Chemistry can be performed on the overhanging 5' or 3' transposon ends to increase the size of library elements or enable binding to beads or other biomolecules. A variety of transposon designs and modifications may be used to increase the physical size of library fragments.

For example, a transposon with a 3' overhang may be used to tagment DNA. The 3' overhang can serve as a substrate for the enzymes. Terminal transferase (TdT) can be used to add a certain number of bases in a template independent manner. For example, TdT may be used to add 100-300 bases to the transposon. If TdT transposon extension is not sufficient, the elongated transposon could be hybridized to oligo-bound beads present in the polymer beads, a complimentary amplicon, or poly-A tailed cellular mRNA. If hybridized to an oligonucleotide, an extension reaction may be performed. For example, if a ssDNA plasmid is annealed, a rolling circle amplification (RCA) reaction could be performed to increase the size of transposon ends. Hybridized oligonucleotides can alternatively be ligated to transposon ends. Successive ligation of amplicons, such as in Cycle Ligation Assembly (CLA), could be performed to assemble long stretches of DNA from smaller fragments capable of diffusing into the polymer beads.

Addition of modified bases to transposons could also be used as targets for binding of additional molecules. The modified bases could be present in the transposon prior to tagmentation or be added enzymatically post-tagmentation. For example, TdT could be used to add the modified base Digoxigenin-11-UTP, which can later be bound by anti-DIG antibody. Other modifications include biotin and 5mC, which can bind to streptavidin and 5mC antibodies, respectively.

In some embodiments, simultaneous indexing of gDNA fragments and cDNAs originating from the same polymer bead and additional amplification of library elements may be performed by rolling circle amplification.

EXAMPLES

Example 1—Preparation of Polymer Beads

The following example demonstrates an embodiment of preparing polymer beads encapsulating long DNA fragments using microfluidic droplet generators.

A droplet generator was used to generate the polymer beads. Samples containing long DNA fragments were mixed with polymer precursor and the mixture was loaded into a sample reservoir on a cartridge. Within 2 minutes, around 50,000 polymer beads containing long DNA were generated from each channel (8 channels for 8 independent sample processing each cartridge. The long DNA polymer beads were loaded onto a flow cell, where polymer beads stuck inside (100 μm high channel and 120 μm polymer beads diameter) for hands-free library preparation. Enzymes and reagents, including nucleic acid library preparation enzymes and reagents, were introduced to the flow cell, contacting the long DNA embedded inside the polymer bead, and cleaving the long DNA molecules through tagmentation to form a DNA library. The library was then seeded on the flow cell from the beads. During library seeding, oil was loaded to fill the void between beads and the flow cell was heated to accelerate diffusion of the library onto the flow cell surface. In the presence of the oil, seeding of each tagmented library occurred in close proximity to the footprint of each polymer bead (from 120 µm diameter polymer beads, library seeding is limited to a roughly 120 µm diameter area).

This Example demonstrates that long DNA molecules could be loaded and trapped in polymer beads (about 120 µm in diameter) and library preparation performed on these long DNA molecules embedded inside the polymer beads. As a result, all DNA libraries from a specific long DNA molecule were stored within the same polymer beads. The library was then released from the polymer beads to the flow cell surface to seed them as a group on the flow cell surface. The clusters released from a long DNA molecule grouped together as a "cluster patch" on the flow cell. Clusters inside a single patch from a single long DNA molecule simplifies reconstruction of the genome with higher accuracy and fewer scaffolding gaps.

Example 2—Long DNA Spatial Indexing

The following example demonstrates an embodiment of strobed reads of long DNA fragment of 100 kb encapsulated within a polymer bead with or without MDA.

Figure 5:
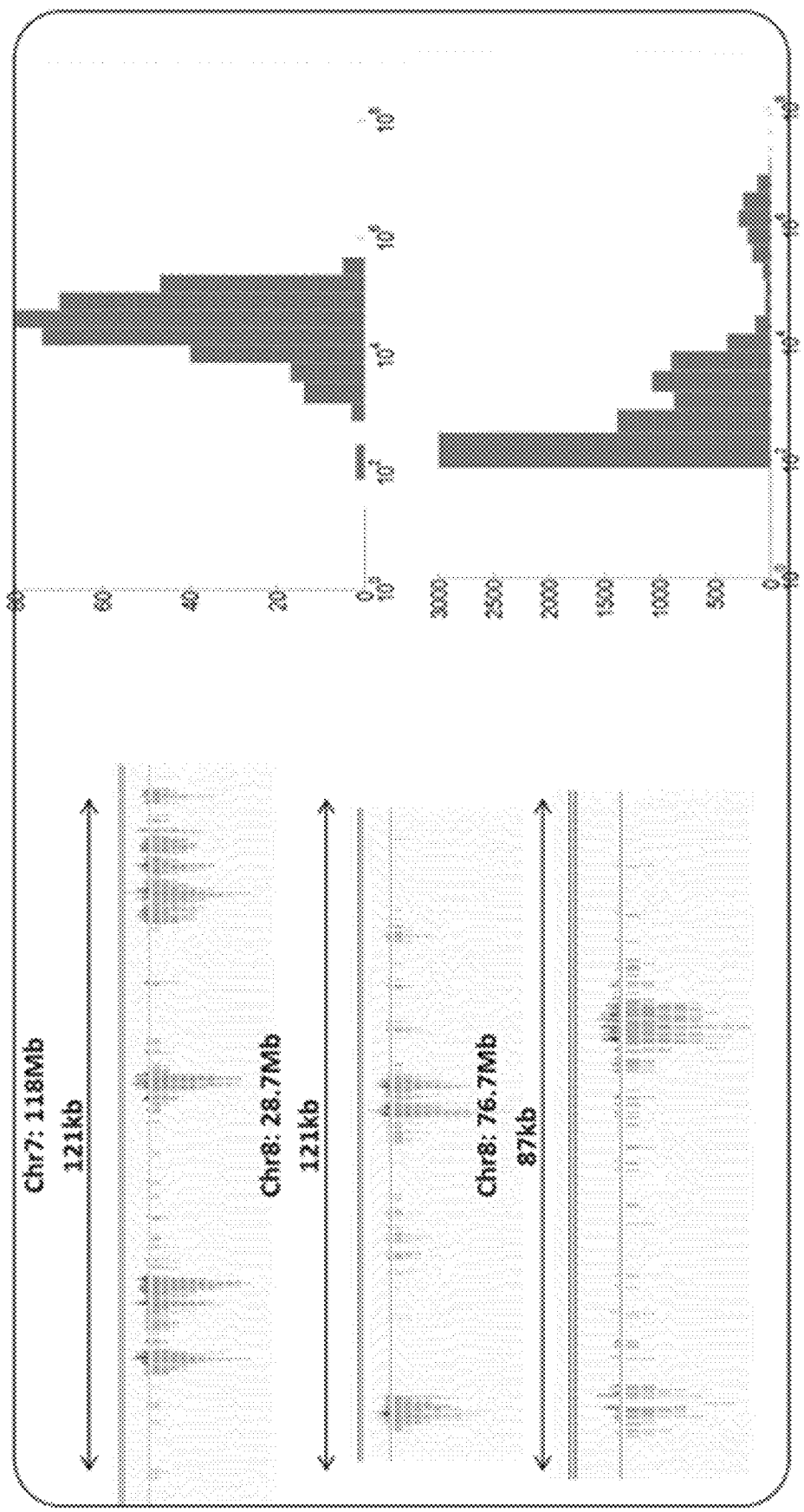
FIG. 5 shows a line graph of linked reads of long DNA hydrogel spatial indexing on 100 kb DNA fragments with MDA.

Polymer beads were prepared by mixing a polymer in the presence of Corriell genomic DNA of about 100 kb and forming polymer beads using a microdroplet generator. The DNA was subjected to spatial indexing sequencing by placing the formed polymer beads encapsulating the DNA fragments on a flow cell device, and contacting the flow cell with reagents. No MDA was performed. The beads were degraded and clusters formed on the flow cell device. As shown in FIG. 5, the average clusters per long DNA island was about 33, the average long DNA island size was 64000 base pairs, and there were about 405 long DNA islands per bead.

Figure 6:
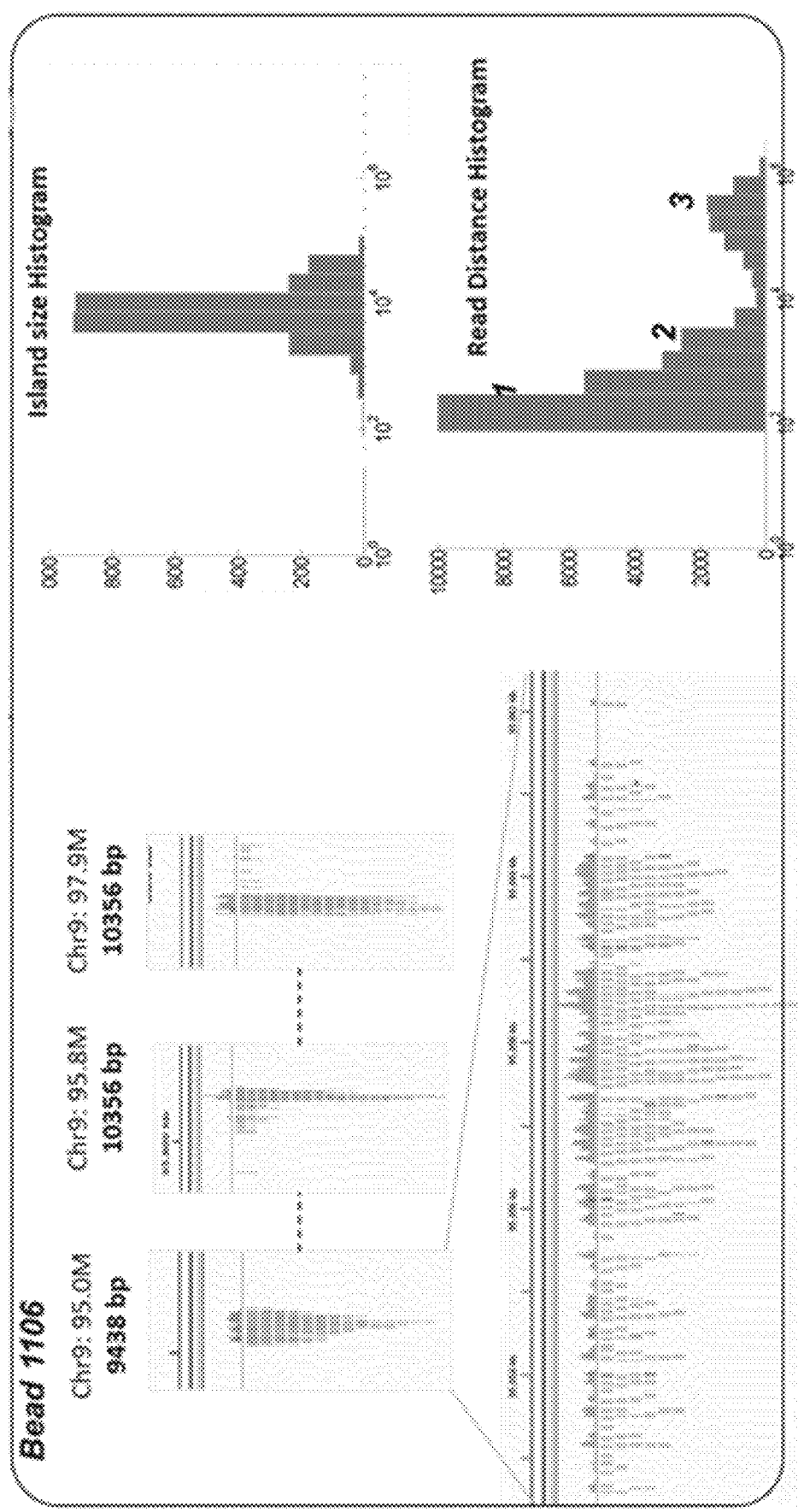
FIG. 6 shows a line graph of linked reads of long DNA hydrogel spatial indexing on 10 kb DNA fragments with MDA.

A second set of polymer beads were prepared by mixing a polymer in the presence of Corriell genomic DNA of about 100 kb and forming polymer beads using a microdroplet generator. The DNA was subjected to spatial indexing sequencing by placing the formed polymer beads encapsulating the DNA fragments on a flow cell device, and contacting the flow cell with reagents. MDA was performed prior to tagmentation. The beads were degraded and clusters formed on the flow cell device. As shown in FIG. 6, the average clusters per long DNA island increased to about 85, the average long DNA island size was 58000 base pairs, and there were about 166 long DNA islands per bead.

A third set of polymer beads were prepared by mixing a polymer in the presence of Corriell genomic DNA of about 10 kb and forming polymer beads using a microdroplet generator. The DNA was subjected to spatial indexing sequencing by placing the formed polymer beads encapsulating the DNA fragments on a flow cell device, and contacting the flow cell with reagents. MDA was performed prior to tagmentation. The beads were degraded and clusters formed on the flow cell device. As shown in FIG. 7, the average clusters per long DNA island was about 57, the average long DNA island size was 10461 base pairs, and there were about 85 long DNA islands per bead.

Example 3—Metagenomics on Complex Mixture of Microbial Species

The following example demonstrates an embodiment of identifying single cell microbes encapsulated within a hydrogel.

Polymer beads were prepared as described herein using a microfluidics microdroplet generator. The polymer material was mixed with a sample containing a number of microbes, including *L. gasseri, S. aureus, B. cereus, B. vulgatus, A. baumannii, S. agalactiae*, and *P. acnes*. The encapsulated cells were then lysed and subjected to library preparation, whereupon the polymer beads were degraded and the libraries deposited on a surface. As shown in FIG. 9, each microbe was capable of being identified due to its spatial compartmentalization on the flow cell device. Thus, the encapsulating and subsequent nucleic acid reactions enable strain-level identification of microbial species in complex mixtures using reads compartmentalization in a mini-metagenomics assay.

Example 4—On Flow Cell Spatial Indexing

The following example demonstrates an embodiment for on-flow cell spatial indexing.

A flow cell device was obtained and washed with 200 µl PR2 (incorporation buffer). Beads for processing were also washed with PR2. A diluted hydrogel was prepared in PR2. Increased dilution results in increased spacing between hydrogels. The hydrogel was embedded on the flow cell, and the introduction of air bubbles to the flow cell was avoided. 200 µl PR2 was flowed through the flow cell to ensure beads remained fixed to go through the process. 100 µl RSB was flowed through the flow cell.

A tagmentation mix was prepared by mixing 25 µl tagmentation reagent, 23 µl RSB, and 2 µl enzyme. The tagmentation mix was introduced to the narrow channel to remove any possible air bubble on the inlet. The tagmentation mix was then flowed slowly to the inlet. The flow cell was sealed and incubated for 10 min at 55° C.

A stop buffer mix was prepared by mixing 25 µl tagmentation buffer, 25 µl RSB, and 10 µl stop buffer. The stop buffer mix was slowly flowed onto the flow cell without introducing any bubbles, and incubated at room temperature for 5 mins. After incubation, 200 µl of PR2 was flowed through the device.

NPM was prepared by mixing 175 µl RSB and 75 µl NPM. The NPM mix was slowly flowed onto the flow cell device without introducing any air bubble, and incubated for 3 mins at room temperature. 200 µl of oil with surfactant was flowed onto the flow cell device. Micrographs revealed that the hydrogels were surrounded with NPM mix and oil. The flow cell was sealed and incubated for 3 mins at 72° C. for gap filling reaction.

20-30 µl of oil with surfactant and oil with DTT (29/2 ratio) were flowed onto the flow cell device, and the device was sealed. The start temperature release process was 90° C. for 3 mins, 60° C. for 5 mins, 40° C. for 2 mins, and 20° C. for 2 mins. The flow cell was washed with 400 µl PR2, and 200 µl CLM (cleavage mix). The flow cell was then washed with 400 µl PR2. Where phix seeding is desired, a Phix was prepared with 2-3 µM concentration, and the phix library was flowed onto the device, and incubated at room temperature for 5 mins. The flow cell was washed with 200 µl PR2.

100-200 μl AMX for 1st extansion was flowed, and incubated for 5 min at 50° C. The flowcell was washed with PR2, and a 24 or 30 cycle amplification was performed.

Example 5—Simultaneous Indexing of gDNA Fragments and cDNAs

The following example demonstrates an embodiment for simultaneous indexing of gDNA fragments and cDNAs from the same polymer bead.

Polymer beads were prepared as hollow polymer shells having a cell encapsulated therein. About 25 to 50 polymer beads were distributed into wells of a microtiter plate and were treated with cell lysis buffer to disrupt cellular membrane followed by gDNA transposition with indexed Y adapter transposome, formed with transposons phosphorylated at the 5' end of both strands. Terminal transferase (TdT) was added to add multiple Ts to the 3' end of the non-transfer strand, allowing hybridization to a polyA tail of mRNA.

The gap between gDNA and non-transfer strand of transposon was performed by a filling and ligating reaction, and cDNA synthesis was performed by MMLV reverse transcriptase (RT). MMLV RT also added a few additional dCMPs bases to the 3' end of cDNA molecule, which base paired with oligoG sequence at the 3' end of template switching primer (TSP). Annealed TSP was extended and its sequence was transferred to the 3' end of newly synthesized cDNA in template switching reaction. Formed gDNA-cDNA hybrid contained three different common sequences, one on each end and one in the middle of the strand, separating gDNA and cDNA portions of the hybrid molecule. These common sequences were used for both gDNA and cDNA libraries preparation.

Figure 13A:
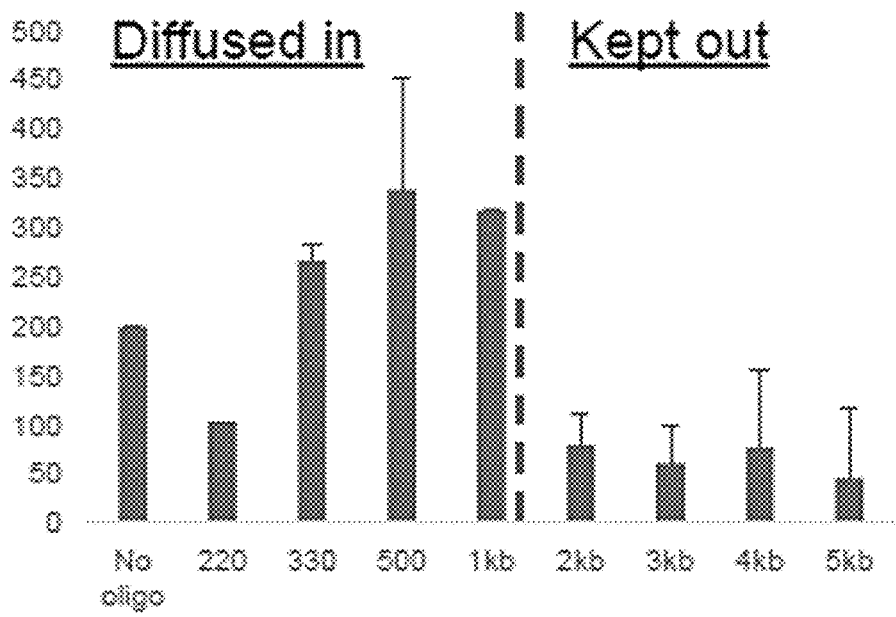
FIGS. 13A and 13B illustrate graphs showing diffusion of nucleic acid into a polymer bead as a function of nucleic acid size. Graphs represent entrance of small amplicons (220 bp-1 kbp) inside polymer beads while longer amplicons do not diffuse into the polymer beads.
Figure 13B:
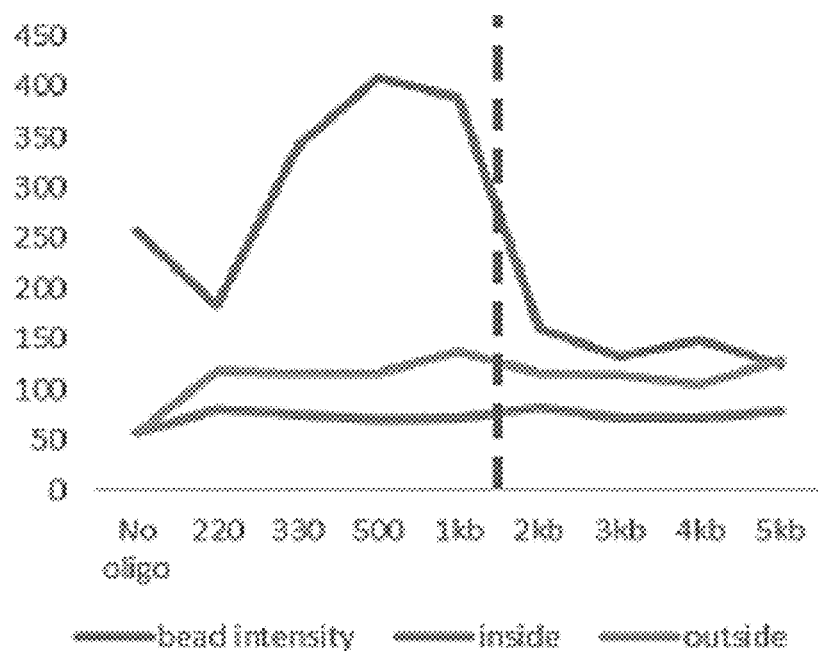

In a side reaction, the extension of mRNA and template switching at the 3'end of transposons was observed, but these activities did not affect the outcome. After RNAse H treatment and brief washes, the content of the polymer beads were heat denatured and subjected to circle ligation reaction. During this reaction, all single stranded DNA molecules with phosphorylated 5' end self-ligated into circles, which became templates for rolling circle amplification (RCA). In addition to the gDNA-cDNA hybrid, individual tagmented DNA as well as cDNA molecules produced from mRNA annealed to free floating transposomes were also circle ligated and amplified in RCA reaction. Long concatemers contain multiple copies of starting molecules increased sensitivity of the assay, and were retained inside the polymer beads.

dsDNA of approximately <1 kbp in length can pass through polymer beads for a 15% PEG-MAL hollow polymer bead. Briefly, streptavidin coated beads (approx. 10 μm in diameter) were encapsulated inside the polymer beads. Following this, biotinylated amplicons of different size were allowed to diffuse into the polymer beads. A threshold diffusion limit representing the molecular size cut-off was determined over a variable amplicon size range (eg: 220 bp-5000 bp), as shown in FIGS. 13A-13B.

Figure 14:
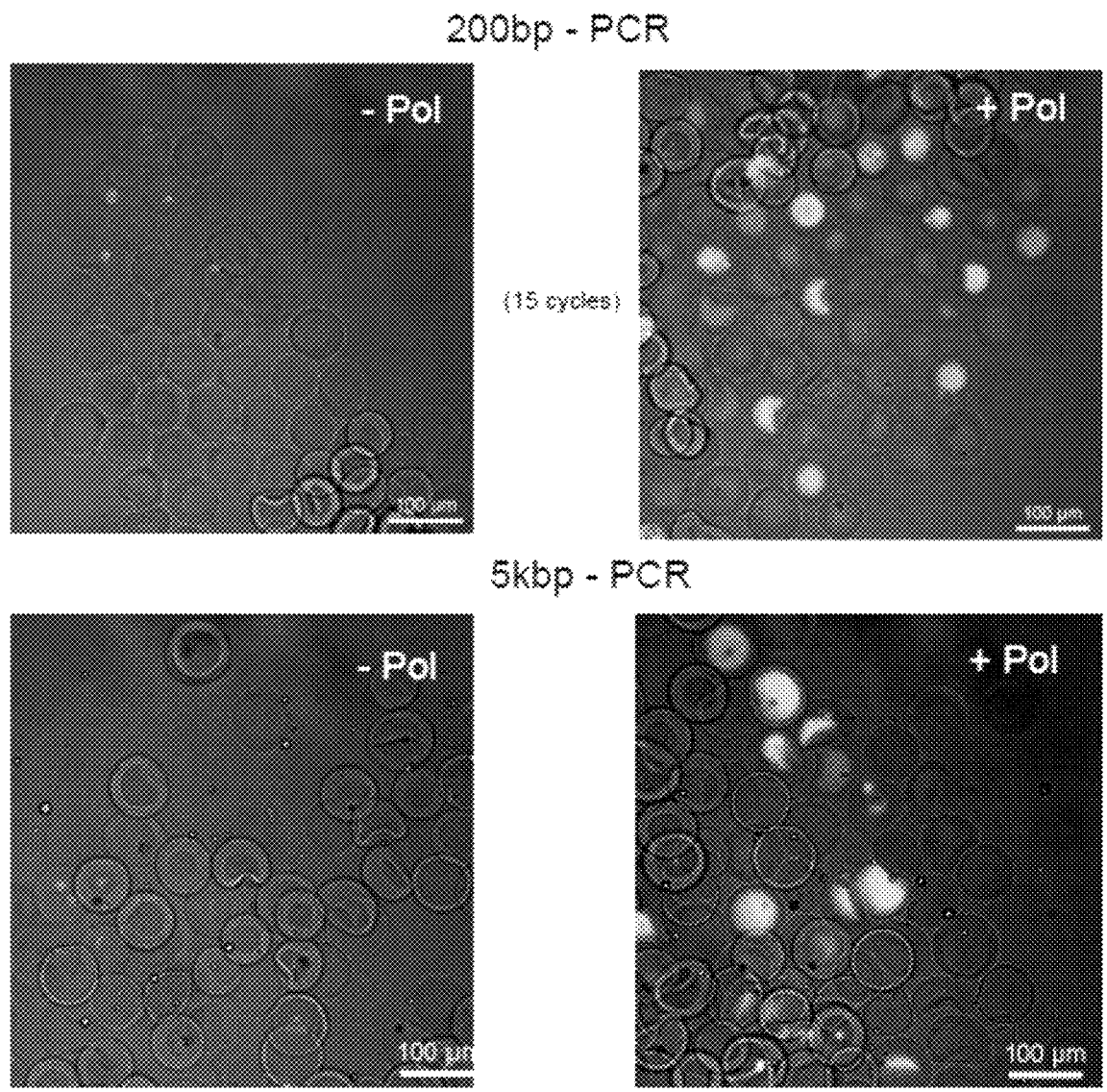
FIG. 14 depicts micrographs of porous hollow beads, showing PCR-based amplification inside the porous hollow beads for both 200 base pair and 5000 base pair DNA fragments.

Similarly, to test the compatibility of polymerase chain reactions and retainability of genomic products, a containment model was designed where amplicon bound polymer beads (using biotin-streptavidin conjugation chemistry) were loaded into the polymer beads. Linear amplification of these variable sized amplicon on beads not only suggest that the polymer beads are PCR compatible but were able to determine the retainability of molecules for 200 bp and 5 kbp amplified DNA fragments. 200 bp products can diffuse into surrounding polymer beads, whereas 5 kbp products are maintained within the polymer beads (FIG. 14).

In addition to biomolecular assays that can increase the size of products to retain small molecules, polymer beads can be composed of multilayered polymers which can have controlled diffusion of molecules based on charge, pH, temperature, or other environmental factors (FIG. 15). Examples of such systems can include materials such as ionic and non-ionic polymers including alginate, polyethylene glycol, N-isopropylacrylamide, N,N'-dimethylacrylamide, or other polymer described herein.

Example 6—Polymer Beads with Sacrificial Cores

The following example demonstrates an embodiment for preparing polymer beads having a sacrificial core.

Figure 16A:
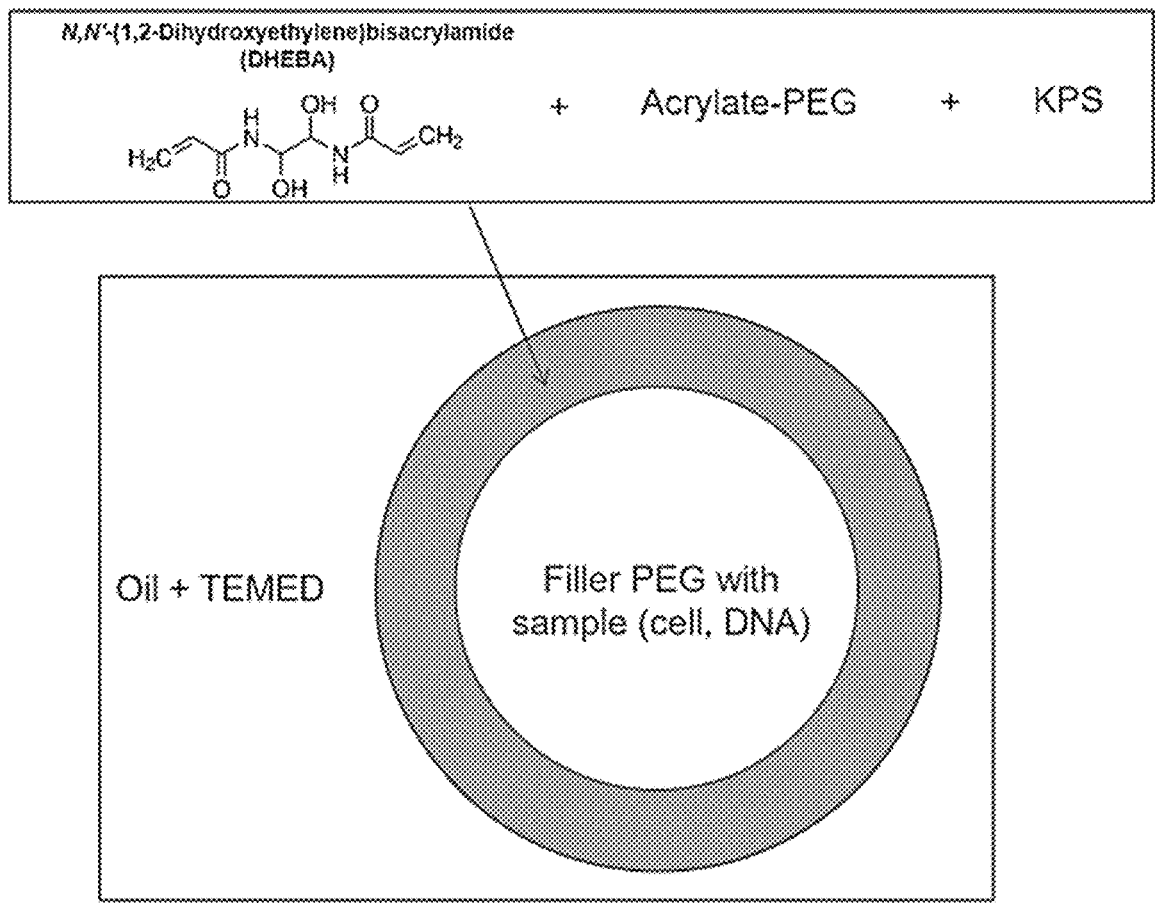
FIGS. 16A-16C depict polymer beads having a stabilized shell with a sacrificial polyacrylamide core.
Figure 16B:
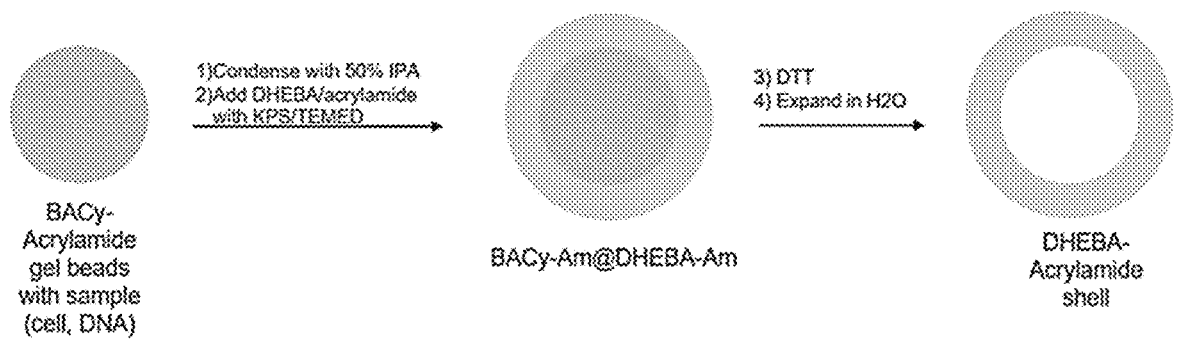
Figure 16C:
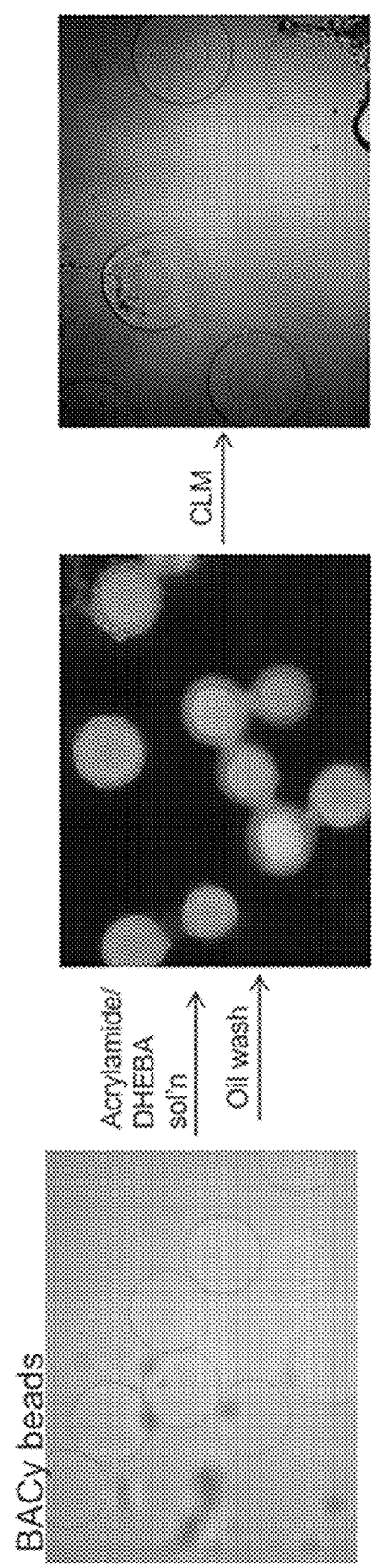

A core having a sacrificial polymer was prepared with the sample (cells or DNA). The core included a filler, such as PEG or polyacrylamide that was mixed with the sample to form a polymer bead, as shown in FIG. 16A. The bead was condensed with 50% isopropyl alcohol (IPA), and mixed with DHEBA/acrylamide with KPS/TEMED (FIG. 16B). The result was a polymer bead encapsulated with a DHEBA shell. The DHEBA shell is unstable at temperatures used for dehybridization and seeding, resulting in a release of the core from the DHEBA shell at high temperatures. Further, treatment of the DHEBA polymer bead with a reducing agent, such as DTT, and expansion in water, resulted in a DHEBA-acrylamide shell. FIG. 16C depicts micrographs of DHEBA polymer beads, corresponding to the schematic representation shown in FIG. 16B.

Figure 17A:
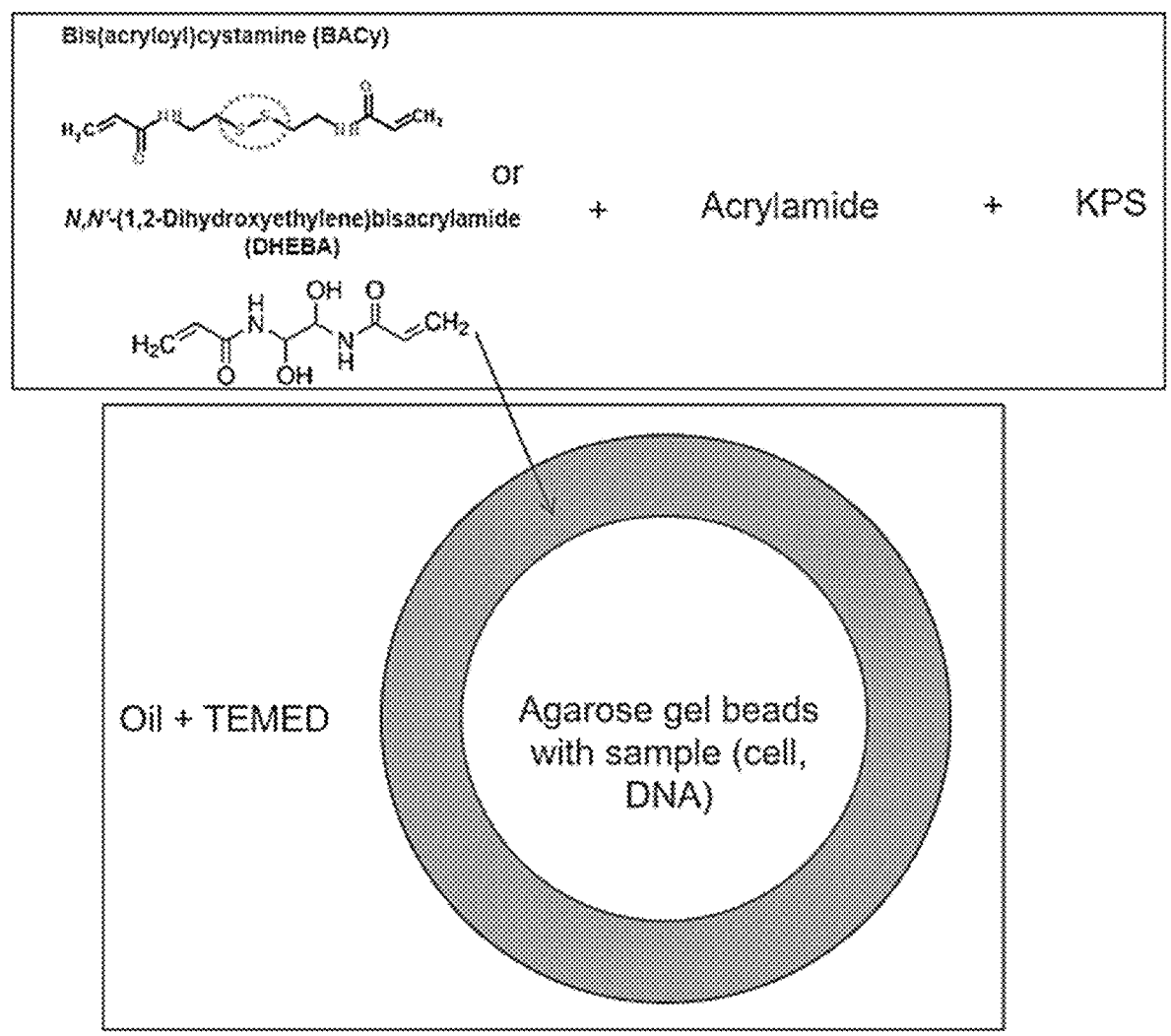
FIGS. 17A-17C depict polymer beads having a stabilized shell with a sacrificial agarose core.
Figure 17B:
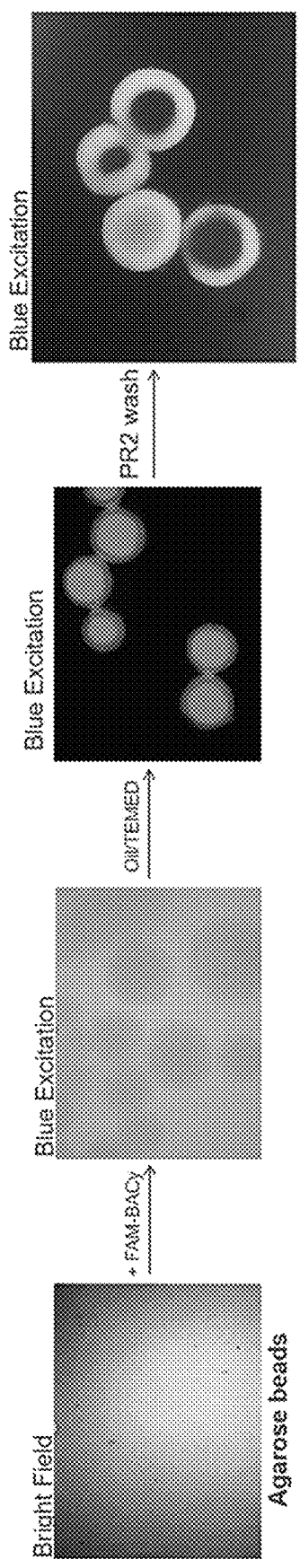
Figure 17C:
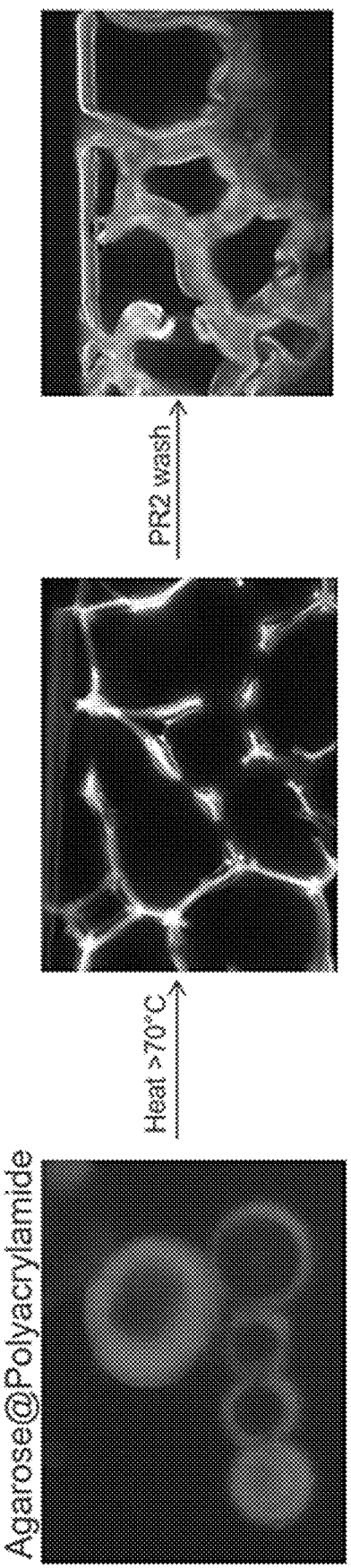

Another embodiment is a polymer bead having a DHEBA shell with an agarose core, as shown in FIG. 17A. The agarose core bead was prepared in a fashion similar to the polyacrylamide core bead. A sample of cells or DNA was mixed with agarose to form a polymer bead, using a method as described herein. The agarose beads can be functionalized and used to purify the sample, such as DNA. The polymer bead was contacted with DHEBA, which encapsulated the polymer bead, as shown in FIG. 17B. UV may be used to initiate construction of the DHEBA shell around the polymer bead. The agarose core was subjected to temperature or chemical digestion to melt the core, resulting in a hollowed DHEBA shell, as shown in FIG. 17C.

Example 7—Fluorescence Initiation Gelation of Polymer Beads

The following example demonstrates an embodiment for preparing polymer beads using a fluorescence initiation gelation method.

Figure 18A:
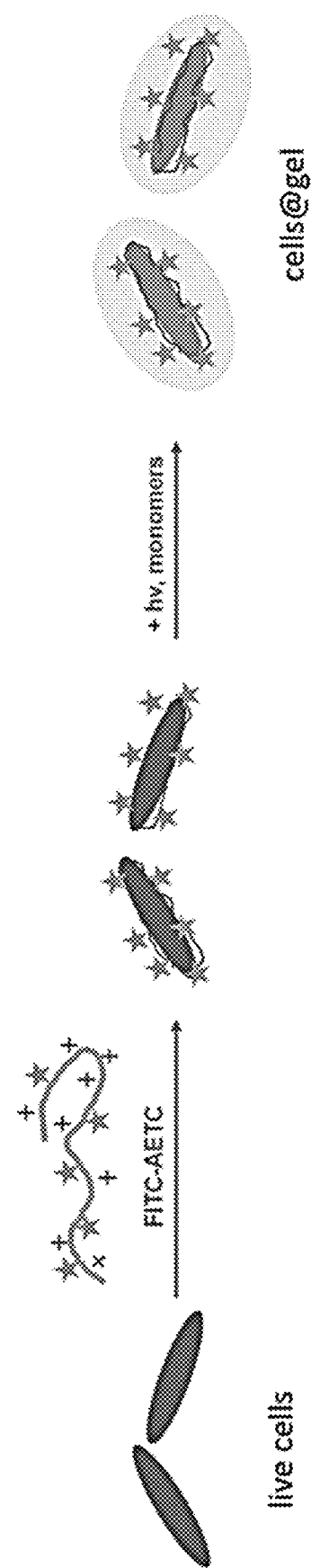
FIGS. 18A-18C depict fluorescence initiated gelation.
Figure 18B:
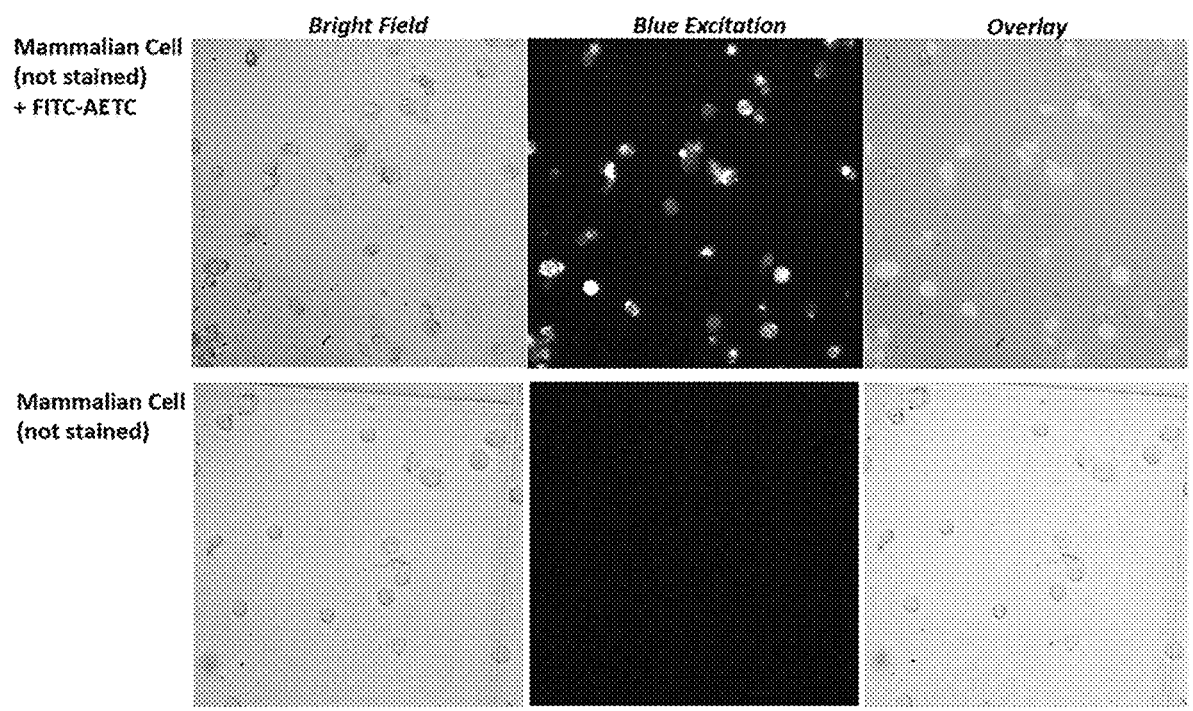
Figure 18C:
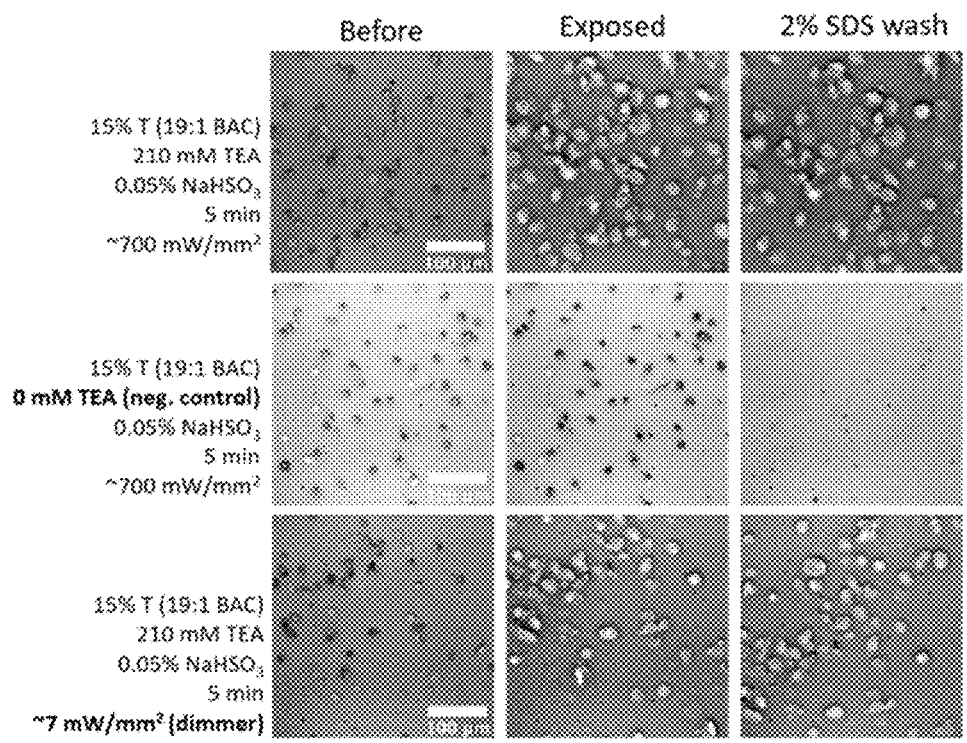

A sample, such as cells or DNA were obtained. The sample was contacted with a polymer having fluorescein isothiocyanate (FITC) bound acrylate polymers (FITC-AETC), which coated the sample. The FITC-AETC bound samples were contacted with radiation, such as light radiation and monomers, which resulted in FITC-bound cells within a polymer gel, as shown schematically in FIG. 18A. The resulting cells can be imaged without staining due to the FITC interaction on the cell surface, as shown in FIGS. 18B and 18C. Control samples that were not coated in FITC-AETC did not display excitation. The fluorescein-initiated gelation described herein may be performed in solution. When performed in solution, polymerization initiated in the center of a bulk solution droplet. Triethanolamine (TEA) was added in an amount of 210 mM to initiate gelation. Also added was 0.05% $NaHSO_3$.

The embodiments, examples, and figures described herein provide compositions, methods, and systems for retaining biomolecules in physically confined space during the process from lysis to library generation. Some embodiments provide libraries originated from single long DNA molecule or a single cell to be released on a surface of a flow cell in confined space. Once the library from a single DNA molecule or single cell in the individual compartments are released to the surface of the flow cell, the library from each compartment gets seeded at close proximity to each other.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A solid support comprising a plurality of beads, wherein each bead comprises:
   a hydrogel polymer precursor;
   a crosslinker; and
   a biomolecule disposed within each bead, wherein each bead is a porous hollow bead that comprises multiple polymer layers, wherein each polymer layer comprises at least one of a distinct pore size and a distinct pore density that allows diffusion of a reagent through the bead while retaining the biomolecule.

2. The solid support of claim 1, wherein the solid support is a flow cell device.

3. The solid support of claim 2, wherein the flow cell device comprises a patterned surface.

4. The solid support of claim 2, wherein the flow cell device comprises wells, grooves, or patterns.

5. The solid support of claim 4, wherein the wells have a diameter ranging from about 10 μm to about 50 μm.

6. The solid support of claim 1, wherein the biomolecule is derived from a single cell.

7. The solid support of claim 1, wherein the porous hollow bead comprises 1 to 10 distinct polymer layers.

8. The solid support of claim 1, wherein the pore size is a sufficient size to allow diffusion of molecules ranging from less than 100 base pairs to less than 1000 base pairs through the polymer layer.

9. The solid support of claim 1, wherein the pore density ranges from 0.5 to 0.99 porosity.

10. The solid support of claim 1, wherein the pore size of each polymer layer is specifically modulated based on charge, pH, or temperature.

11. The solid support of claim 1, wherein each bead has a diameter of about 50 μm to about 150 μm.

12. The solid support of claim 1, wherein the hydrogel polymer precursor comprises polyethylene glycol (PEG)-thiol/PEG-acrylate, PEG/maleimide (PEG/MAL), acrylamide/N,N'-bis(acryloyl)cystamine (BACy), N,N'-(1,2-dihydroxyethylene)bisacrylamide (DHEBA), PEG/polypropylene oxide (PPO), polyacrylic acid, poly (hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, or collagen.

13. The solid support of claim 1, wherein the crosslinker comprises bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate.

14. The solid support of claim 1, wherein the biomolecule is a nucleic acid.

15. The solid support of claim 14, wherein the nucleic acid is a long DNA molecule of 50,000 base pairs or greater.

16. The solid support of claim 1, wherein the reagent comprises enzymes, chemicals, and primers having a size of less than 50 base pairs.

17. The solid support of claim 1, wherein the reagent comprises lysozyme, proteinase K, random hexamers, polymerase, transposase, primers, ligase, catalyzing enzyme, deoxynucleotide triphosphates, buffers, or bivalent cations.

18. The solid support of claim 1, wherein the bead further comprises a stabilized shell that encapsulates the bead.

19. The solid support of claim 18, wherein the stabilized shell comprises N,N'-(1,2-dihydroxyethylene)bisacrylamide (DHEBA), acrylate-PEG, and potassium peroxydisulfate (KPS).

20. A method of preparing a nucleic acid library, comprising:
    introducing a plurality of beads to a flow cell device, wherein each bead comprises:
    a hydrogel polymer precursor;
    a crosslinker; and
    a biomolecule disposed within each bead, wherein the bead is a porous hollow bead that comprises multiple polymer layers, wherein each polymer layer comprises at least one of a distinct pore size and a distinct pore density that allows diffusion of a reagent through the bead while retaining the biomolecule,
    introducing nucleic acid library preparation enzymes to the flow cell device;
    forming a DNA library from the biomolecule within each bead; and
    releasing the DNA library onto the flow cell device.

21. The method of claim 20, wherein releasing the DNA library comprises increasing the temperature of the flow cell device.

22. The method of claim 20, wherein the biomolecule is a long DNA molecule of 50,000 base pairs or greater.

23. The method of claim 20, wherein forming a DNA library comprises performing a tagmentation reaction.

24. The method of claim 20, further comprising spatial indexing of DNA.

* * * * *

UNITED STATES PATENT AND TRADEMARK OFFICE
CERTIFICATE OF CORRECTION

PATENT NO. : 11,999,945 B2
APPLICATION NO. : 17/305230
DATED : June 4, 2024
INVENTOR(S) : Steven Norberg et al.

Page 1 of 2

It is certified that error appears in the above-identified patent and that said Letters Patent is hereby corrected as shown below:

On the Title Page

Page 3, Column 2 item (56) (Other Publications), Line 15, delete "transposone" and insert -- transpososome --.

Page 3, Column 2 item (56) (Other Publications), Line 45, delete "second-generaiton" and insert -- second-generation --.

In the Specification

Column 7, Line 9, delete "(D29" and insert -- Φ29 --.

Column 7, Line 55, delete "trimethylopropoane" and insert -- trimethylolpropane --.

Column 7, Line 57, delete "tetracrylate," and insert -- tetraacrylate, --.

Column 9, Line 29, delete "(D29" and insert -- Φ29 --.

Column 12, Line 33, delete "zymolose," and insert -- zymolyase, --.

Column 14, Line 44, delete "(D29" and insert -- Φ29 --.

Column 14, Line 67, delete "contiguity preserving" and insert -- contiguity-preserving --.

Column 14, Line 67, delete "(CPTSeq)" and insert -- (CPT-Seq) --.

Column 16, Line 60, delete "O-methylphosphoroamidite" and insert -- O-methylphosphoramidite --.

Column 17, Line 9, delete "acylic" and insert -- acrylic --.

Signed and Sealed this
Seventeenth Day of September, 2024

Katherine Kelly Vidal
*Director of the United States Patent and Trademark Office*

CERTIFICATE OF CORRECTION (continued)
U.S. Pat. No. 11,999,945 B2

Column 17, Line 57, delete "(Φ29" and insert -- Φ29 --.

Column 20, Line 65, delete "µM" and insert -- pM --.

Column 21, Line 1, delete "extansion" and insert -- extension --.

Column 21, Line 36, delete "3'end" and insert -- 3' end --.

Column 21, Line 37, delete "RNAse" and insert -- RNase --.

In the Claims

Column 26, Line 2, Claim 13, delete "trimethylopropoane" and insert -- trimethylolpropane --.

Column 26, Line 4, Claim 13, delete "tetracrylate." and insert -- tetraacrylate. --.